United States Patent [19]

Naparstek

[11] 4,217,641
[45] Aug. 12, 1980

[54] CORRECTION FOR POLYCHROMATIC X-RAY DISTORTION IN CT IMAGES

[75] Inventor: Abraham Naparstek, Shelton, Conn.

[73] Assignee: U.S. Philips Corporation, New York, N.Y.

[21] Appl. No.: 901,212

[22] Filed: Apr. 28, 1978

[51] Int. Cl.$^2$ .................. G01N 23/00; G01T 1/16
[52] U.S. Cl. .................. 364/414; 250/445 T; 358/166; 364/515; 364/571
[58] Field of Search ............ 364/414, 571, 415, 515, 364/527; 250/445 T; 358 R, 360; 358/160, 166

[56] References Cited

U.S. PATENT DOCUMENTS

| | | | |
|---|---|---|---|
| 3,927,318 | 12/1975 | Macovski | 250/445 T |
| 3,944,830 | 3/1976 | Dissing | 250/358 R |
| 3,965,358 | 6/1976 | Macovski | 250/445 T |
| 4,029,963 | 6/1977 | Alvarez et al. | 364/515 |
| 4,063,074 | 12/1977 | Wagner | 364/414 |
| 4,069,422 | 1/1978 | Hounsfield | 260/445 T |

*Primary Examiner*—Errol A. Krass
*Attorney, Agent, or Firm*—Thomas A. Briody; William J. Streeter; Jack E. Haken

[57] ABSTRACT

A method and apparatus which corrects the polychromatic distortion of CT images which is produced by the non-linear interaction of body constituents with a polychromatic X-ray beam. A CT image is processed to estimate the proportion of the attenuation coefficients of the constituents in each pixel element. A multiplicity of projections for each constituent are generated from the original image and are combined utilizing a multidimensional polynomial which approximates the non-linear interaction involved. An error image is then generated from the combined projections and is subtracted from the original image to correct for the polychromatic distortion.

16 Claims, 3 Drawing Figures

CORRECTION FOR POLYCHROMATIC X-RAY DISTORTION IN CT IMAGES

This invention relates to methods and apparatus for computed tomography. More specifically, this invention relates to image processing apparatus which corrects for polychromatic distortion in images produced by the method of computed tomography.

BACKGROUND OF THE INVENTION

Machines for producing transverse images of body sections by the methods of computed tomography are known, for example, for U.S. Pat. Nos. 3,778,614 and 3,924,129 which are incorporated herein, by reference, as background material. In such apparatus one or more beams of penetrating radiation, typically X-rays, are projected through the body in a plurality of directions and are measured, typically with electronic radiation detectors, to yield a multiplicity of projections of internal body structures. The projections are then combined typically in a digital computer using, for example, a convolution-backprojection technique, to generate images of transverse sections through the body.

Early methods for computing the transverse image from its projections generally assumed a linear relationship between the lengths of the various constituents and the total attentuation of these constituents so that the integrated tissue density along the path was equal to the logarithm of the ratio of the radiation intensity entering and exiting the body. This assumption, although generally true for a monochromatic radiation source, produces aberrated images if utilized in a scanner having a polychromatic radiation spectrum in conjunction with body constituents having attenuation coefficients which vary with radiation energy. Prior art scanners have included filters for hardening the X-ray beam (to reduce its low energy spectral content) to partially eliminate polychromatic effects. Many prior art scanners have also attempted to compensate for polychromatic effects by effectively assuming a single attenuation function for all body tissues and applying that function, in conjunction with a known spectrum from the X-ray source, as a first order compensation in the image reconstruction calculations (single spectrum or one dimensional corrections).

Virtually all human body tissues are found to have energy dependent X-ray attenuation characteristics which are dominated by the characteristics of water (soft tissues) and bone and can be approximated by a combination of these characteristics. The energy attenuation spectra of water and bone are, however, substantially different. A polychromatic radiation beam propagating through a body which comprises a mixture of bone and soft tissue (on either a macroscopic or microscopic level) will necessarily be influenced by the combined spectra of calcium and water, which interact in a non-linear fashion to distort X-ray intensity values in the measured projections.

SUMMARY OF THE INVENTION

The method and apparatus in the present invention operate on an original CT image which has no correction for polychromatic X-ray distortion or only a rough pre-reconstruction correction (i.e. a single spectrum correction) applied to the original projection data. The method determines an error image based on information extracted from the original distorted image. The error image is subtracted from the original image to obtain a corrected image. The following steps are involved in obtaining the corrected image:

Estimates of the projections of the various biological tissues (e.g. bone and soft tissue) are obtained artificially from the original digitized image to the extent that these various tissues can be distinguished by means of their grey levels and by a priori geometric and other structural knowledge of the anatomical section that corresponds to the image;

Error projections are calculated from the projections of the various biological tissue using a precalculated polynomial in as many variables as there are distinguishable biological tissues. The precalculated polynomial is determined by using the X-ray energy spectrum of the X-ray source in the scanning apparatus at the particular kilovoltage at which the original projection measurements were made and the linear attenuation coefficients of the biological tissues as a function of energy in such a way as to enforce a multidimensional linear relationship between the integrated attenuation and the equivalent lengths of the distinguishable tissues through which the X-ray beam passes. If a pre-reconstruction correction was made on the original projection data, then the precalculated multidimensional polynomial is modified to take this pre-reconstruction correction, if any, into account;

The error projections are then filtered to remove ripple that is contributed by the projection of a digitized image;

From the error projections an error image is reconstructed by means of either the same reconstruction process that was used to produce the original image or by some other reconstruction process of sufficient accuracy;

The original image and the error image are then subtracted, pixel by pixel, to obtain a corrected image.

It is, therefore, an object of the invention to correct polychromatic distortion in computed tomographic images.

Apparatus for performing the methods of the invention comprises:

means for analyzing the values in an original image array and for assigning to each pixel element a specific proportion of the attenuation coefficient of two or more constituent tissues;

Means for combining the proportions of said attenuation coefficients to generate a multiplicity of constituent projections for each of said constituents;

Means for combining said constituent projections to generate an error image wherein the value of each pixel represents the difference between a pixel value in the original image and that pixel value in a corrected image; and Means for subtracting the error image from the original image to generate a corrected image.

The method and apparatus of the present invention thus operate to produce an error image which is subtracted from an original image rather than reconstructing a corrected image from corrected projections. Quantization noise and reconstruction artifacts which might otherwise affect the quality of a corrected image reconstructed from corrected projections are thus reduced.

DESCRIPTION OF THE PREFERRED EMBODIMENT

Figure 1:
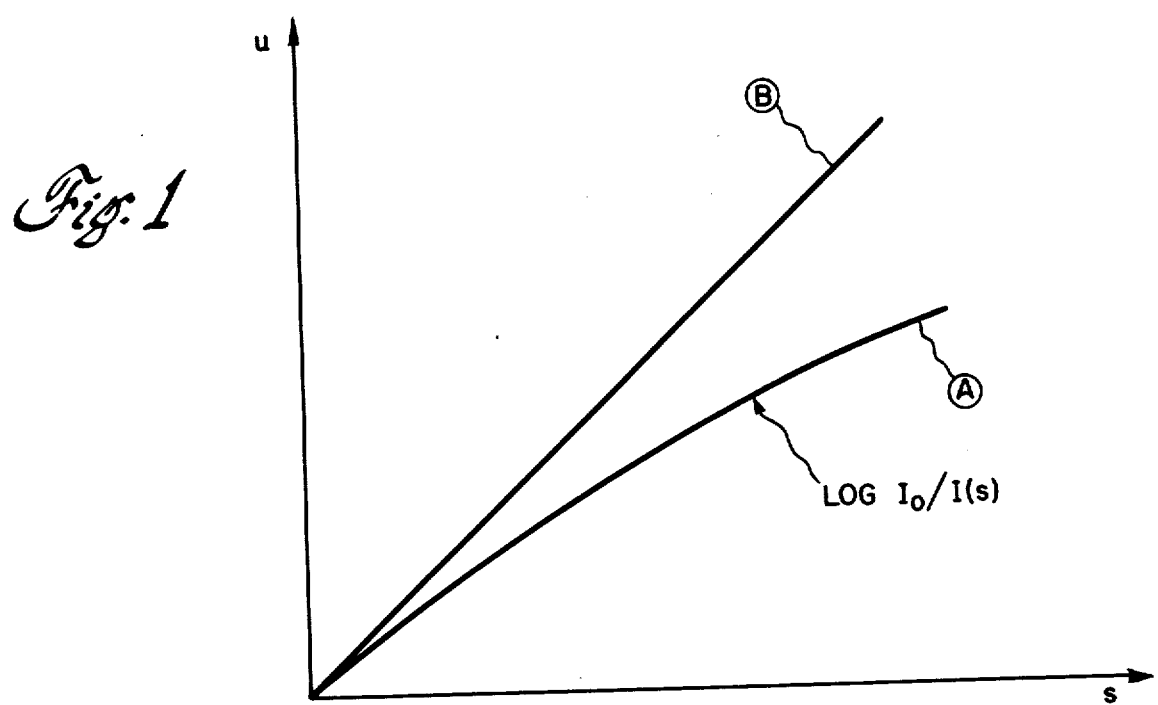
FIG. 1 illustrates the attenuation of a polychromatic X-ray beam in a homogeneous material.

It is known that for an object consisting of a single homogeneous material, such as calcium or water, the X-ray attenuation function has a shape in the form of curve A in FIG. 1. This function depends on the incident radiation spectrum and on the type of homogeneous material. Its departure from linearity results from the shift and change of the shape of the photon energy spectrum as photons of different energy undergo different attenuation in passing through the same length of material. In FIG. 1, the initial slope B of the curve may be considered as the incremental linear X-ray attenuation coefficient associated with the polychromatic X-ray beam. When such an X-ray beam passes through a composite material made up of two or more distinct homogeneous materials the attenuation is a non-linear function of the lengths of the materials and is not a sum of individual functions of single variables.

Experience indicates that the X-ray attenuation of human body structures may be characterized by the attenuation of a heterogeneous structure of soft tissues (having a water-like energy attenuation spectrum) and bone (having a "compact bone"-like spectrum). Additional body structures may, in fact, comprise air or other gases, but the attenuation of such structures is so low, compared with bone and soft tissue, that its energy spectrum has an insignificant effect on image calculation. The non-linear interaction of bone and soft tissue in the attenuation of a polychromatic X-ray beam may be expressed by a power series of the form $$U(s_1,s_2) = c_{10}s_1 + c_{01}s_2 + c_{20}s_1^2 + c_{02}s_2^2 + c_{11}s_1s_2 +$$

$$c_{30}s_1^3 + c_{03}s_2^3 + c_{12}s_1s_2^2 + c_{21}s_1^2s_2 + \ldots +$$

$$c_{N0}s_1^N + \ldots + c_{0N}s_2^N + \ldots$$

The interaction may be expressed in the form $$U(s_1,s_2) = L(s_1,s_2) +$$

$$T(s_1,s_2) + \epsilon(s_1,s_2),$$

where s c $$T(s_1,s_2) = c_{20}s_1^2 + c_{02}s_2^2 + c_{11}a_1s_2 +$$

$$c_{30}s_1^3 + c_{03}s_2^3 + c_{12}s_1s_2^2 + c_{21}s_1^2s_2 +$$

$$111 + c_{N0}s_1^N + \ldots + c_{0N}s_2^N$$

is a two-dimensional polynomial of degree N, and $L(s_1,s_2)$ is the linear part of the function $U(s_1s_2)$. By choosing the criterion for approximation properly, and the degree N of the polynomial and sufficiently high, $\epsilon(s_1,s_s)$ may be made sufficiently small for calculation purposes, so that $T(s_1,s_2)$ is the correction which must be applied to compensate for the non-linear part of the interaction. Experience indicates that a two-dimensional cubic correction $$T(s_1,s_2) = c_{20}s_1^2 + c_{02}s_2^2 +$$

$$c_{11}s_1s_2 + c_{30}s_1^3 + c_{03}s_2^3 + c_{12}s_1s_2^2 + c_{21}s_1^2s_2 \text{ is}$$
satisfactory for use with human images.

The interaction of an X-ray beam with a heterogeneous material may be approximated by numerical integration using known spectra for the various constituents of the material and measured energy spectrum data for a particular X-ray source operating at a particular voltage. Attenuation coefficients for water and compact bone are, for example, tabulated in the publication "Photon Cross-sections, Attenuation Coefficients, and Energy Coefficients from 10 KeV to 100 GeV" by J. H. Hubbell, National Bureau of Standards, National Standard Reference Data Series NSRDS-NBS 29, Issued August 1969. Energy spectrum data for a particular X-ray source is normally obtained by direct measurement of each type source at its expected operating voltages. The coefficients of the cubic approximation are calculated using any of the well known approximation algorithms. Typically a set of coefficients will be calculated in advance for each X-ray source and operating voltage and stored for later use with raw images measured at the same spectral parameters. By way of example, Table I tabulates the measured energy spectrum area $J(E)\Delta E$ for a Tomoscan 200 CT scanner (manufactured by Philips Medical Systems, Incorporated of Shelton, Connecticut, which utilizes a Philips beryllium window X-ray tube) measured at 150 KVP with a three millimeter thick aluminum filter inserted in the beam. Corresponding attenuation coefficients for compact bone ($\mu_{CB}$) and for water ($\mu_{H2O}$) are also tabulated. Table II is a listing of a Fortran IV computer program for calculating the polynomial coefficients by a suitable least squares approximation, and Table III are the corresponding coefficients calculated thereby from the data of Table I. The coefficients listed in Table III are utilized in the further examples of image correction methods set forth below.

Figure 2:
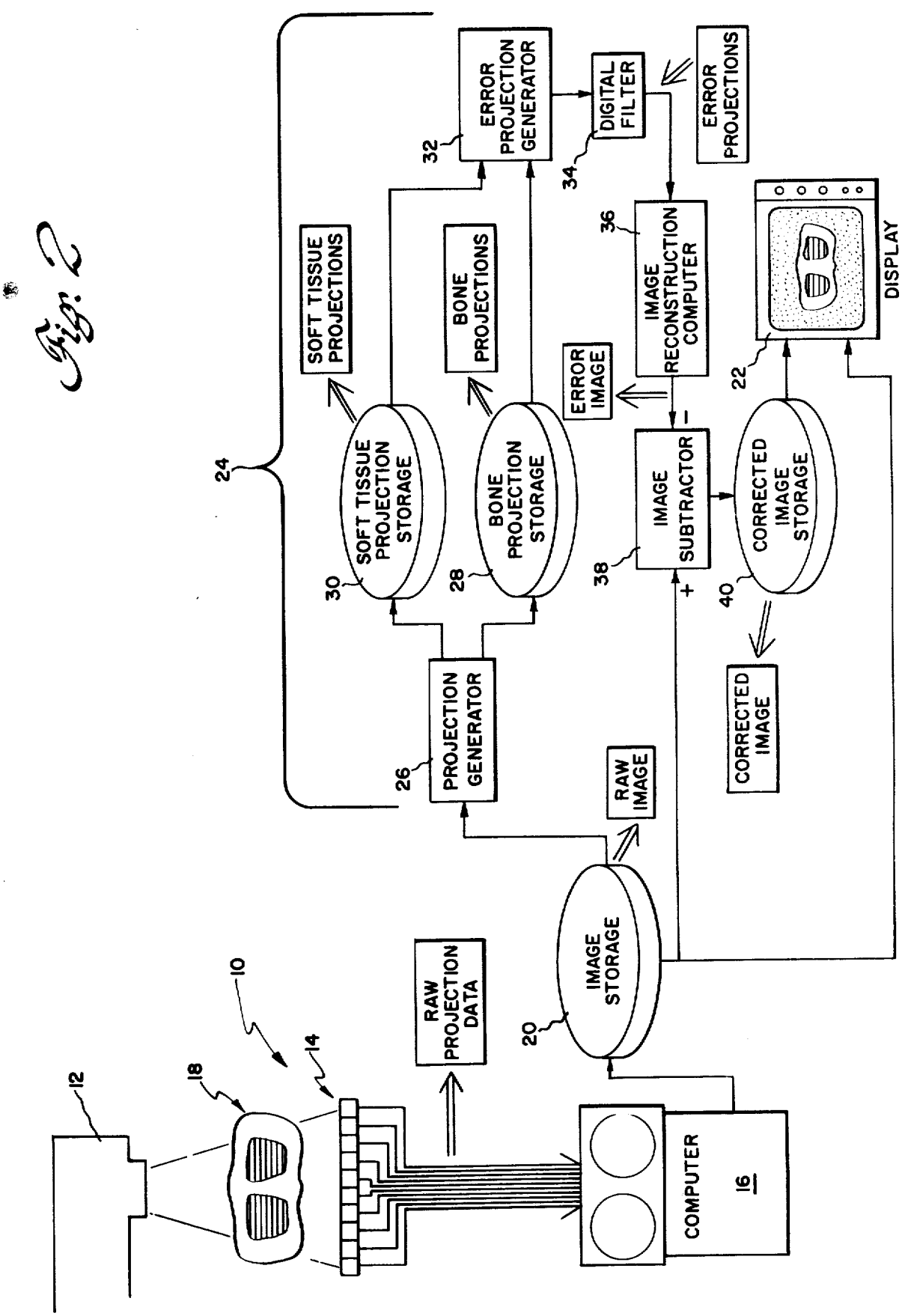
FIG. 2 is an image correction system of the present invention.

FIG. 2 is apparatus for correcting images in accordance with the invention. A computerized tomographic scanner 10 which includes an X-ray source 12, a detector bank 14 and an image reconstruction computer 16 functions, in accordance with the methods of the prior art, to project X-rays through a body 18 along a plurality of beam paths to measure and record a series of X-ray projection data taken through the body 18 from a plurality of directions and to subsequently combine those projections, using any of the known image reconstruction algorithms, to produce a matrix of discrete element of a transverse image of the body wherein the numerical values of the elements represent the intensity in corresponding pixels of the transverse image. The matrix of image elements is stored in an image storage device 20, which may, for example, comprise core memory or disc storage. The raw image may be directly displayed, as in prior art scanners, on a display device 22.

In accordance with the present invention the raw transverse image matrix produced by the computer 16 and stored in the image storage 20 is processed in an image correction processor 24 to compensate for polychromatic aberration. A projection generator 26 functions to assign relative proportions of the attenuation coefficient to soft tissue and compact bone in each pixel element represented in the image storage 20. The mixture of soft tissue and bone represented in each pixel of the raw image may correspond to a macroscopic combination of bone and soft tissue structures lying within the pixel area or may, alternately, represent an intimate mixture as in varying bone or cartilage structures. The assignment of a proportion of the attenuation coefficient to bone and soft tissue in each pixel element may be based on a pattern recognition process and known structural details of the raw image, but is most readily accomplished by a multiple thresholding process which assigns a percentage of the attenuation coefficient to compact bone, soft tissue, or contrast media in each pixel element. For example, experience indicates that all pixels having a grey scale level L greater than 100 Hounsfield units may be assumed to contain bone and that the percentage of the attenuation coefficient due to bone and soft tissue in such elements may be approximated by a linear interpolation of the grey scale value, relative to the upper and lower thresholds for soft tissue and compact bone, respectively.

A value of grey level due to soft tissue and bone content is thus assigned to each pixel of the raw image and is used to generate sets of separate projections of soft tissue and bone from the raw image data. The projections thus generated correspond to a decomposition of the projections which were measured by the scanner 10 and were utilized for the original image reconstruction, and the process of generating projections of soft tissue and bone from the raw image in the image storage 20 is the mathematical adjoint of the operation of backprojection used to generate the raw image from the scanner convolved projection data in the computer 16. There are, of course, many algorithms and methods for generating images from projections and it is not necessary that the process for generating bone and soft tissue projection sets from the raw image correspond to the exact adjoint in the algorithm used in the scanner 10 to generate the raw image from the scanner projection data.

Figure 3:
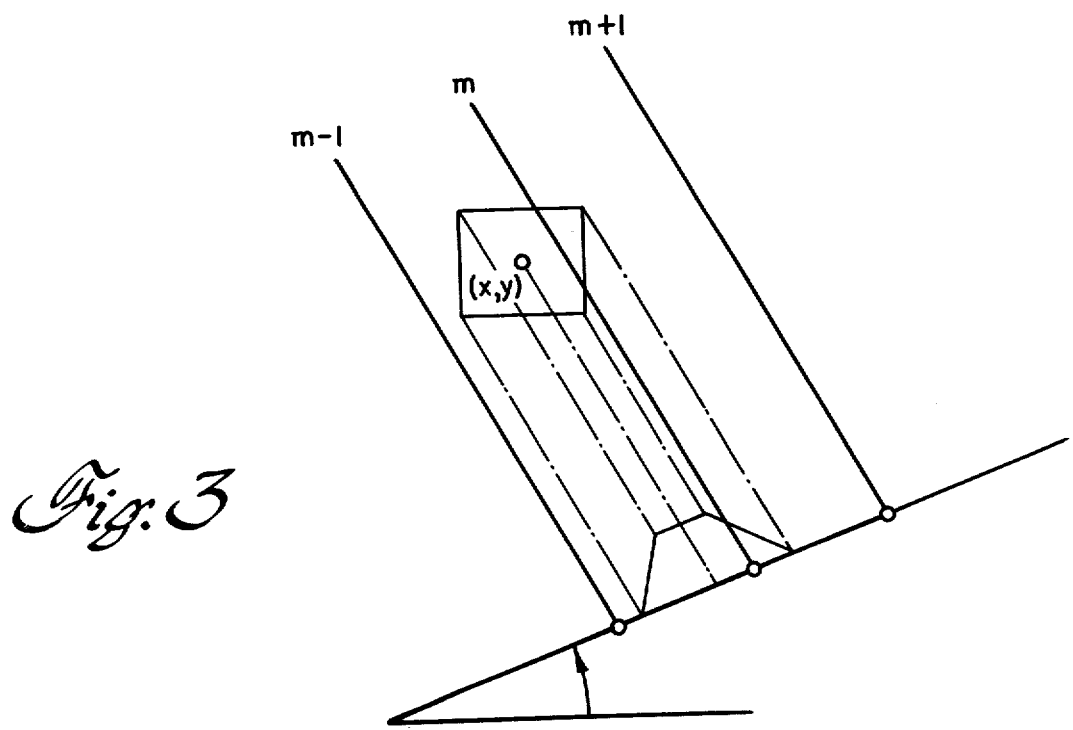
FIG. 3 illustrates a method for projecting pixel elements.

FIG. 3 illustrates a preferred method for generating projections of bone or soft tissue from an image matrix and is related to the so-called strip method employed in itterative reconstruction algorithms. It can be implemented in a manner similar to that of backprojection either in a general purpose digital computer or in a dedicated hardware array processor. For each projection angle $\phi$ a series of equally spaced rays are assumed through the picture matrix and each pixel is assigned to that ray, m, nearest to its center (x,y). The values of the pixel elements assigned to each ray are then summed, the set of sums being the projection at the angle $\phi$ corresponding to the ray direction. Other projection methods, for example direct projection or Fourier transform projection, are also suitable. By way of example, Tables IV and V are preferred embodiments of machine language computer programs, for operation on PDP 11 series computers, which function to threshold raw image data and generate soft tissue and bone projections, respectively, from that data.

The projection generator 26 thus produces two sets of projection data. A first set corresponds to a plurality of projections, at different angles through the image plane, of the bone or calcium structures in the raw image and is stored in a bone projection storage 28 which may, for example, comprise core memory or disk storage. A second set describes corresponding projections of the soft tissue structures in the raw image and is stored in a second storage area 30.

The bone projections stored in device 28 and the soft tissue projections stored in device 30 are then combined in an error projection generator 32 which utilizes a precalculated polynomial, determined in the manner described above from the X-ray spectrum of the source 12 and the linear attenuation coefficients of the biological tissues, as a function of energy, to calculate projections of polychromatic aberration errors in the raw image data.

If a single-spectrum type pre-reconstruction correction for energy spectrum effects was made during the calculation of the raw image data in the computer 16 the pre-calculated polynomial is modified to take into account this pre-reconstruction correction.

The error projection generator 32 may comprise a dedicated hardware processor or may comprise a general purpose digital computer programmed to calculate the error projections from the soft tissue projection and the bone projection data. By way of example, Table VI is a Fortran language computer program which performs the error projection generator function. The calibration coefficient and system coefficient at lines 20 and 25 of the program are scaling factors related to the particular scanner 10 utilized to generate the raw data and have values of 5,000 and 614 respectively for a Tomoscan 200 scanner. The coefficients at lines 12–18 of the correspond to the polynomial coefficients in Table III calculated for the Tomoscan 200 operating at 150 KVP. Lines 31–38 of the program compensate for the single-spectrum pre-reconstruction correction applied in the Tomoscan 200 scanner. The actual computation of the polynomial value is accomplished at line 66.

The error projections produced by the projection generator 32 are filtered in a digital filter 34 to remove noise which inherently results from the projection of a quantized image. The digital filter 34 is, ideally, tuned to the projection generator 26. A preferred embodiment for use with a projection generator described above comprises a three point averaging filter in cascade with an interpretive filter. The interpretive filter functions, for each data point in the projection, to take the average value of increasingly large sets of points surrounding the data point (i.e. three points, five points, seven points . . . ) until the difference between the data point value and the surrounding average value is less than a predetermined threshold. The filter will not, however, increase or decrease the number of points in the averaging set by more than one point for adjacent data points.

The digital filters described above may be implemented as dedicated hardware units or as program modules in a general purpose digital computer. By way of example, Table VII is a Fortran lanugage program for the three point averaging filter described above while Table VIII is a Fortran language program for the interpretive filter. The filtered error projections from the digital filter 34 are then combined in an image reconstruction computer 36 to produce an error image data set which corresponds, on an element by element basis, to the polychromatic distortion error in the raw image in the image storage 20. The image reconstruction computer 36 may be functionally identical to the image reconstruction function in the computer 16 which computes the raw image from the X-ray projections measured by the scanner 10 and may, thus, comprise any of the hardware or software image computers which are known and described in the prior art.

The error image produced by the image reconstruction computer 36 is then subtracted, on a point by point basis, from the raw image held in image storage 20; the function being preformed in an image subtractor 38. The corrected image thus produced is fully compensated for polychromatic distortion and is held in a corrected image storage device 40 for subsequent display on the display device 22. By way of example, Table IX is a Fortran language computer program which may be utilized to preform the function of the image subtractor 38. As will be recognized by those skilled in the art, the image subtractor 38 may, alternately, comprise a hardware digital subtractor.

Although the preferred embodiments of the invention have been described herein with individual components corresponding to program modules for execution in a general purpose digital computer, it should be recognized that, in a given dedicated system, increases in speed and efficiency may be derived by constructing some or all of the individual components as dedicated digital hardware. It will likewise be recognized that the specific construction of these individual components is necessarily highly dependent on the nature and organization of other computing and data storage components in the system but that the methods for producing such hardware from the software embodiments set forth herein are well known. Further, although the present system utilizes a two-dimensional polynomial to compensate for two tissue constituents, a higher dimensional polynomial may similarly be utilized to compensate for other tissue constituents or contrast media.

TABLE I

| E (KEV) | J(E)ΔE (RELATIVE ENERGY UNITS) | $\mu CB$ (cm$^{-1}$) | $\mu H_2O$ (cm$^{-1}$) |
|---|---|---|---|
| 20 | .007453 | 5.47950 | 0.769 |
| 25 | .057012 | 3.61832 | 0.566 |
| 30 | .152612 | 1.75695 | 0.363 |
| 35 | .256730 | 1.37085 | 0.313 |
| 40 | .342131 | 0.98475 | 0.263 |
| 45 | .419619 | 0.82875 | 0.2435 |
| 50 | .477813 | 0.67275 | 0.244 |
| 55 | .500218 | 0.60060 | 0.214 |
| 60 | .529548 | 0.52845 | 0.204 |
| 65 | .510852 | 0.49725 | 0.1987 |
| 70 | .460579 | 0.46605 | 0.1935 |
| 75 | .425318 | 0.43485 | 0.1882 |
| 80 | .397156 | 0.40365 | 0.183 |
| 85 | .367806 | 0.39000 | 0.180 |
| 90 | .335680 | 0.37635 | 0.177 |
| 95 | .312675 | 0.36270 | 0.174 |
| 100 | .279061 | 0.34905 | 0.171 |
| 110 | .556958 | 0.33735 | 0.167 |
| 120 | .345380 | 0.32565 | 0.163 |
| 130 | .227633 | 0.31395 | 0.159 |
| 140 | .119441 | 0.30225 | 0.155 |

TABLE II

```
FORTRAN IV      / V01B-02A                                    PAGE 001
CORE=08K,  UIC=[101,101]                                      ,LP/SP=POLY

C       PROGRAM POLYCHROME
        C
        C       THIS PROGRAM COMPUTES THE COEFFICIENTS OF A 2-DIMENSIONAL
        C       LEAST-SQUARES CUBIC FIT FOR POLYCHROMATIC CORRECTION
        C
        C
0001            DIMENSION ATTEN(16,26),SPECT(23),CB(23),HO(23),
             1     V1(26),V2(26),V3(26),V4(26),V5(26),V6(26),
             2     W1(26),W2(26),W3(26),W4(26),W5(26),W6(26),ATK(26),
             3     DEL(26),DIFF(16,26)
0002            DOUBLE PRECISION COEF(7,8),WORK(7,8,16),X(1,7),A,B
0003            EQUIVALENCE(ATK,V1)
        C
        C
        C       FIRST COMPUTE U(S1,S2)=LOG(I0/I(S1,S2))
        C       AND UCB,UHO
        C
0004            DATA CB/5.47950,3.61823,1.75695,1.37085,0.98475,0.82875,
             1     0.67275,0.60060,0.52845,0.49725,0.46605,0.43485,0.40365,
             2     0.39000,0.37635,0.36270,0.34905,0.33735,0.32565,0.31395,
             3     0.30225,0.55731,0.47853/
        C
        C
0005            DATA HO/0.7690,0.5660,0.3630,0.3130,0.2630,0.2435,0.2240,
             1     0.2140,0.2040,0.1987,0.1935,0.1882,0.1830,0.1800,0.1770,
             2     0.1740,0.1710,0.1670,0.1630,0.1590,0.1550,0.2080,0.1956/
        C
        C
0006            DATA SPECT/0.003726,0.057012,0.152612,0.256730,0.342131,
             1     0.419619,0.477813,0.500218,0.529548,0.519852,0.460579,
             2     0.425318,0.397156,0.367896,0.335680,0.312675,0.418591,
             3     0.445566,0.345380,0.227633,0.119441,0.213402,0.065277/
        C
0007            CALL ASSIGN(1,'SY0:[101,101]POLYX.DAT;1')
0008            DEFINE FILE 1(16,52,U,IU)
        C
        C
0009            SUMB=0.0
0010            SUM1=0.0
```

```
0011        SUM2=0.0
0012        DO 10 I=1,23
0013        SUMB=SUMB+SPECT(I)
0014        SUM1=SUM1+SPECT(I)*CB(I)
0015        SUM2=SUM2+SPECT(I)*HO(I)
0016   10   CONTINUE
0017        CONST=ALOG(SUMB)
0018        UCB=SUM1/SUMB
0019        UHO=SUM2/SUMB
       C
0020        WRITE(6,20) UCB,UHO
0021   20   FORMAT(10X,'UCB=',F8.6,3X,'UHO=',F8.6,///)
0022        DO 90 K=1,16
0023        KP=K-1
0024        JK=26-KP
0025        DO 25 L=1,26
0026   25   ATK(L)=0.0
0027        DO 40 J=1,JK
0028        JP=J-1
0029        SUMT=0.0
0030        DO 30 I=1,23
0031        POWER=CB(I)*KP+HO(I)*JP
0032        FACTOR=EXP(-POWER)
0033        PROD=SPECT(I)*FACTOR
0034        SUMT=SUMT+PROD
0035   30   CONTINUE
0036        U=CONST-ALOG(SUMT)
0037        ATTEN(K,J)=U
0038        ATK(J)=U
0039   40   CONTINUE
0040        WRITE(6,50)K
0041   50   FORMAT(10X,'LINE ',I2;//)
0042        DO 70 IP=1,JK,10
0043        WRITE(6,60)(ATK(J),J=IP,IP+9)
0044   60   FORMAT(3X,10(F9.6,3X))
0045   70   CONTINUE
0046        WRITE(1'K)(ATK(J),J=1,26)
       C
0047        WRITE(6,80)
0048   80   FORMAT(///)
0049   90   CONTINUE
       C    NEXT COMPUTE THE COEFFICIENTS IN THE
       C    LINEAR EQUATIONS FOR LEAST-SQUARES 2-D CUBIC FIT
0050        DO 100 J=1,26
0051        V1(J)=ATTEN(1,J)
0052        V2(J)=V1(J)*V1(J)
0053        V3(J)=V2(J)*V1(J)
0054        V4(J)=V3(J)*V1(J)
0055        V5(J)=V4(J)*V1(J)
0056        V6(J)=V5(J)*V1(J)
0057  100   CONTINUE
0058        DO 200 K=1,16
0059        W1(K)=ATTEN(K,1)
0060        W2(K)=W1(K)*W1(K)
0061        W3(K)=W2(K)*W1(K)
0062        W4(K)=W3(K)*W1(K)
0063        W5(K)=W4(K)*W1(K)
0064        W6(K)=W5(K)*W1(K)
0065  200   CONTINUE
       C
0066        DO 300 M=1,7
0067        DO 300 N=1,8
0068  300   COEF(M,N)=0.0
0069        DO 350 M=1,7
0070        DO 350 N=1,8
0071        DO 350 K=1,16
0072  350   WORK(M,N,K)=0.0
0073        DO 400 K=1,16
0074        JK=27-K
0075        KP=K-1
       C
0076        DO 360 J=1,JK
0077        JP=J-1
0078        DIFF(K,J)=ATTEN(K,J)-UHO*JP-UCB*KP
0079        WORK(1,1,K)=WORK(1,1,K)+V4(J)
0080        WORK(1,2,K)=WORK(1,2,K)+V2(J)*W2(K)
0081        WORK(1,3,K)=WORK(1,3,K)+V3(J)*W1(K)
0082        WORK(1,4,K)=WORK(1,4,K)+V4(J)*W1(K)
0083        WORK(1,5,K)=WORK(1,5,K)+V3(J)*W2(K)
0084        WORK(1,6,K)=WORK(1,6,K)+V5(J)
```

```
0085            WORK(1,7,K)=WORK(1,7,K)+V2(J)*W3(K)
0086            WORK(1,8,K)=WORK(1,8,K)+DIFF(K,J)*V2(J)
0087            WORK(2,2,K)=WORK(2,2,K)+W4(K)
0088            WORK(2,3,K)=WORK(2,3,K)+W3(K)*V1(J)
0089            WORK(2,4,K)=WORK(2,4,K)+W3(K)*V2(J)
0090            WORK(2,5,K)=WORK(2,5,K)+W4(K)*V1(J)
0091            WORK(2,6,K)=WORK(2,6,K)+W2(K)*V3(J)
0092            WORK(2,7,K)=WORK(2,7,K)+W5(K)
0093            WORK(2,8,K)=WORK(2,8,K)+DIFF(K,J)*W2(K)
       C
       C
0094            WORK(3,3,K)=WORK(3,3,K)+V2(J)*W2(K)
0095            WORK(3,4,K)=WORK(3,4,K)+V3(J)*W2(K)
0096            WORK(3,5,K)=WORK(3,5,K)+V2(J)*W3(K)
0097            WORK(3,6,K)=WORK(3,6,K)+V4(J)*W1(K)
0098            WORK(3,7,K)=WORK(3,7,K)+V1(J)*W4(K)
0099            WORK(3,8,K)=WORK(3,8,K)+DIFF(K,J)*V1(J)*W1(K)
       C
0100            WORK(4,4,K)=WORK(4,4,K)+V4(J)*W2(K)
0101            WORK(4,5,K)=WORK(4,5,K)+V3(J)*W3(K)
0102            WORK(4,6,K)=WORK(4,6,K)+V5(J)*W1(K)
0103            WORK(4,7,K)=WORK(4,7,K)+V2(J)*W4(K)
0104            WORK(4,8,K)=WORK(4,8,K)+DIFF(K,J)*V2(J)*W1(K)
0105            WORK(5,5,K)=WORK(5,5,K)+V2(J)*W4(K)
0106            WORK(5,6,K)=WORK(5,6,K)+V4(J)*W2(K)
0107            WORK(5,7,K)=WORK(5,7,K)+V1(J)*W5(K)
0108            WORK(5,8,K)=WORK(5,8,K)+DIFF(K,J)*V1(J)*W2(K)
       C
0109            WORK(6,6,K)=WORK(6,6,K)+V6(J)
0110            WORK(6,7,K)=WORK(6,7,K)+V3(J)*W3(K)
0111            WORK(6,8,K)=WORK(6,8,K)+DIFF(K,J)*V3(J)
       C
0112            WORK(7,7,K)=WORK(7,7,K)+W6(K)
0113            WORK(7,8,K)=WORK(7,8,K)+DIFF(K,J)*W3(K)
0114       360  CONTINUE
0115            DO 370 M=1,7
0116            DO 370 N=M,8
0117       370  COEF(M,N)=COEF(M,N)+WORK(M,N,K)
0118       400  CONTINUE
       C
       C
0119            DO 410 M=2,7
0120            DO 410 N=1,M-1
0121       410  COEF(M,N)=COEF(N,M)
0122            DO 430 M=1,7
0123            WRITE(6,420)(COEF(M,N),N=1,8)
0124       420  FORMAT(3X,8(F13.3,X),///)
0125       430  CONTINUE
0126            WRITE(6,440)
0127       440  FORMAT(///)
0128            DO 500 L=1,7
0129            A=COEF(L,L)
0130            IF(ABS(A).LE.10E-6)GO TO 600
0132            DO 450 N=L,8
0133            COEF(L,N)=COEF(L,N)/A
0134       450  CONTINUE
0135            IF(L.EQ.7)GO TO 500
0137            DO 460 M=L+1,7
0138            B=COEF(M,L)
0139            DO 460 N=L,8
0140            COEF(M,N)=COEF(M,N)-COEF(L,N)*B
0141       460  CONTINUE
0142       500  CONTINUE
       C
0143            DO 520 M=1,7
0144            WRITE (6,510)(COEF(M,N),N=1,8)
0145       510  FORMAT(3X,8(F14.9,X),///)
0146       520  CONTINUE
0147            WRITE(6,530)
0148       530  FORMAT(///)
0149            X(1,7)=COEF(7,8)
0150            DO 550 L=1,6
0151            LP=7-L
0152            S=0.0
0153            DO 540 NP=8-L,7
0154       540  S=S+COEF(LP,NP)*X(1,NP)
0155            X(1,LP)=COEF(LP,8)-S
0156       550  CONTINUE
0157            WRITE(6,560)(X(1,M),M=1,7)
0158       560  FORMAT(15X,7(F12.9,X),///)
```

```
0159            DO 590 K=1,16
0160            KP=K-1
0161            JK=26-KT
0162            DO 565 J=1,JK
0163            JP=J-1
0164            P=X(1,1)*V2(J)+X(1,2)*W2(K)+X(1,3)*V1(J)*W1(K)
              1  +X(1,4)*V2(J)*W1(K)+X(1,5)*V1(J)*W2(K)+X(1,6)*V3(J)+X(1,7)*W3(K)
0165            DEL(J)=DIFF(K,J)-P
0166      565   CONTINUE
0167            WRITE(6,570) K
0168      570   FORMAT(10X,'LINE ',I2,//)
0169            DO 582 IP=1,JK,10
0170            WRITE(6,580)(DEL(J),J=IP,IP+9)
0171      580   FORMAT(3X,10(F9.6,3X))
0172      582   CONTINUE
0173            WRITE(6,584)
0174      584   FORMAT(///)
0175      590   CONTINUE
0176            GO TO 620
0177      600   WRITE(6,610)L
0178      610   FORMAT(10X,'L= ',I1,'COEFICIENT LESS THAN10E-6')
0179      620   STOP
0180            END
```

TABLE III $$T = c_{20}u^2_{H_2O} + c_{02}u^2_{CB} + c_{11}u_{CB}u_{H_2O} + c_{21}u^2_{H_2O}u_{CB} +$$

$$c_{12}u_{H_2O}u^2_{CB} + c_{30}u^3_{H_2O} + c_{03}u^3_{CB}$$

TOMOSCAN 200 AT 150 KVP 3MM Al

| | | |
|---|---|---|
| $c_{20}$ | = | + 0.031142870 |
| $c_{02}$ | = | + 0.122494967 |
| $c_{11}$ | = | + 0.091107809 |
| $c_{21}$ | = | − 0.007675052 |
| $c_{12}$ | = | − 0.010228481 |
| $c_{30}$ | = | − 0.002924285 |
| $c_{03}$ | = | − 0.008226780 |

TABLE IV

```
         .TITLE UNMW250
;TASK WHICH MAKES SOFT TISSUE PROJECTIONS FROM EXISTING 250 SECTOR
;IMAGE.DAT FILE.
;
;GB ARRAYS ARE 512 WORD SECTOR PAIRS ON DK1:,STARTING AT GBSSEC;
;GW ARRAYS ARE 512 WORD SECTOR PAIRS ON DK1:,STARTING AT GWSSEC;
; ONLY THE 1ST 511 WORDS OF EACH PAIR ARE DATA (NSPSMP=511).
;THE INPUT ARRAY IS READ FROM SY0:(LUN 1) AS FILE IMAGE.DAT, AS
; 256 ROWS OF 256 WORDS EACH, STARTING FROM THE TOP ROW OF
; THE PICTURE.
;
; IGP=STARTING ADDRESS OF GW ARRAYS IN CORE
;NOTE: UNMFB IS WRITTEN IN SUCH A WAY THAT OPERAND ADDRESSES
; MAY BE CALCULATED AS IN MF (USING XLIST,ETC). THEREFORE F IS
; GIVEN DOUBLE PRECISION SPACE IN FBUF AND GPBUF1 CONTAINS
; THE LOW 16 BITS OF CALCULATED G-VALUES. THE HIGH 16 BITS ARE
; STORED IN GPBUF2. WHEN THE G VALUES HAVE BEEN CALCULATED,
; THEY ARE CONVERTED TO SINGLE PRECISION IN GPBUF1 & WRITTEN TO
; DK1:.
;
; NSPSMP=# OF ELEMENTS (L VALUES) IN A GB(L,THETA)
; NTHE=# OF THETA VALUES OF GB ARRAYS IN CORE
; IF=STARTING ADDRESS OF F(X,Y) ROWS IN CORE
; NSPUSP=# OF ROWS OR COLUMNS IN F(X,Y)
; NY=# OF Y VALUES OF F(X,Y) IN CORE
; IC=STARTING ADDRESS OF COS*NCM/ACM TABLE
; IS=STARTING ADDRESS OF SIN*NCM/ACM TABLE
; ITH1=INITIAL THETA SUBSCRIPT (FOR 1ST THETA IN CORE)
; IYT=INITIAL (TOP) Y SUBSCRIPT OF F(X,Y) IN CORE
;
; NSPSMP MUST BE ODD; NSPUSP MUST BE EVEN.
; NSPDSP/NY AND NPRJS/NTHE MUST BE INTEGERS
;
        .MCALL  FSRSZ$,FDBBF$,FDICS$,FDOPS$,NMBLK$
        .MCALL  QIOS$,READ$
        .MCALL  FDAT$A,FDEF$A,OPEN$W
        .MCALL  OPENBL,CLOSE$,GET$S,OPEN$
        .MCALL  WISE$S,WTLO$S,EXIT$S,WAIT$
        .LIST   MEB
```

```
000000                    52          R0=%0
000001                    53          R1=%1
000002                    54          R2=%2
000003                    55          R3=%3
000004                    56          R4=%4
000005                    57          R5=%5
000006                    58          SP=%6
000007                    59          PC=%7
                          60
000001                    61          SY0=1
000002                    62          DK1=2
                          63
001000                    64          LGPREC=512.
000777                    65          NSPSAM=511.
000400                    66          NSPDIS=256.
000014                    67          NTHETS=12.
000020                    68          NYS=16.
000034                    69          NPROJS=540.
000030                    70          GSSEC=24.
002129                    71          CPSSEC=2*NPROJS+GSSEC
004210                    72          GRSSEC=2*NPROJS+CPSSEC
006300                    73          GWSSEC=2*NPROJS+GBSSEC
                          74
                          75
000055                    76          NTGRPS=NPROJS/NTHETS
000020                    77          NYGRPS=NSPDIS/NYS
001000                    78          FBYTSC=2*NSPDIS
                          79
                          80
000000                    81          FBUFSZ=4*NSPDIS*NYS
030000                    82          GPD1SZ=2*LGPREC*NTHETS
030000                    83          GPD2SZ=GPD1SZ
014000                    84          XCBFSZ=2*NTHETS*NSPDIS
000000                    85          YSBFSZ=2*NYS*NYS
002070                    86          ICBFSZ=2*NPROJS
002070                    87          ISBFSZ=2*NPROJS
003030                    88          XLSTSZ=2*3*NSPDIS
                          89
                          90          ;USE FBUF AS SCRATCH AREA FOR FCS GETS AT START OF PROGRAM:
                          91          FBUF:
000000                    92          FDBIC:  FSHSZ#  1,512.
000030                    93                  FDBOF#  ,RECBUF,512.
000140                    94                  FDBC9A  RECBUF
000020 000572'            95                  .WORD   512.
000140 001000             96                  FD0F9A  SY0,,ICNAM
       001                97                  .BYTE   SY0
000046 000140'            98                  .WORD   ICNAM
                          99
                         100
```

```
101 000120              IGNAM:  NMBLK$  IG.DAT
    000146      034270          .RAD50  /IG/
    000150      000000          .WORD   0
    000152      000000          .WORD   0
    000154      014474          .RAD50  /DAT/
102
103 000176              FDBIS:  FDBDF$
104 000226      000572          FDRC5A  ,RECBUF,512.
    000230      010000          .WORD   RECBUF
    000232                      .WORD   512.
105 000246              ;       FDOP2A  SY0,,ISNAM
    000244      001             .BYTE   SY0
106 000336      000336          .WORD   ISNAM
    000344      035474          NMBLK$  IS,DAT
    000346      000000          .RAD50  /IS/
    000350      000000          .WORD   0
    000352      014474          .WORD   0
                                .RAD50  /DAT/
107
108 000374              FDDXL:  FDBDF$
109 000534      000572          FDRC3A  ,RECBUF,512.
    000416      010000          .WORD   RECBUF
    000414                      .WORD   512.
    000436              ;       FDOP2A  SY0,,XLNAM
110 000442      001             .BYTE   SY0
    000534      000534          .WORD   XLNAM
111 000542      113751          XLNAM:  XLIST,DAT
    000546      000000          .RAD50  /XLIST/
    000550      014474          .WORD   0
                                .RAD50  /DAT/
112
113 000572              RECBUF: .BLKB   512.
114                     ;
115                     ;
116 000572      040000          =FBUF+FBUFSZ
117 040000              GPBUF1: .BLKB   GPB1SZ
118 070000              GPBUF2: .BLKB   GPB2SZ
119 120000              XCBUF:  .BLKB   XCBFSZ
120 134000              YSBUF:  .BLKB   YSBFSZ
121 136600              ICBUF:  .BLKB   ICBFSZ
122 136670              ISBUF:  .BLKB   ISBFSZ
123 140760              XLBUF:  .BLKB   XLSTSZ
124
125
126 143760              FDBIMG: FBBDF$
127 144120      000C            FBAT2A  R.FIX,FD.BLK,512.,-258.
    143760      000C            .BYTE   R.FIX
    143761                      .WORD   FD.BLK
    143762      001000          .WORD   512.
    144014      177376          .WORD   -250.
128 144120      0000            FDRC3A  FD.RWM,FBUF,512.
    144002      000000          .BYTE   FD.RWM
    144000      010000          .WORD   FBUF
                                .WORD   512.
```

```
129  144120  000000'         FDBK9A:  FDBUF,512.,,3,SB3
     144002  001000                   .WORD    FDBUF
     144000  003                      .WORD    512.
     144004  147730'                  .BYTE    3
                                      .WORD    SB3
130  144020  001                      .BYTE    SY0,,IMGNAM,FO.RD
     144022  144120'                  .BYTE    SY0
     144026  000C                     .WORD    IMGNAM
                                      .BYTE    FO.RD
131  144120  026210         IMGNAM:   NMBLK$   IMAGE,DAT,1
     144126  035111                   .RAD50   /IMAGE/
     144132  000000                   .WORD    0
     144134  014474                   .RAD50   /DAT/
     144136  000001                   .WORD    1

;
;MACRO TO LOAD A BUFFER WITH CONSTANTS FROM DISK:
132                           .MACRO  LOAD$  FDB,BFSIZ,BFSA
133                           MOV     FDB,R0      ;FILE DESCRIPTOR BLOCK ADR
134                           MOV     BFSIZ,R1    ;SIZE (BYTES) OF DEST BUFFER
135                           MOV     BFSA,R2     ;STARTING ADR OF DESTINATION
136                           JSR     PC,RDNWDS
137                           LOAD$
138                           .ENDM
139  ;
140  ;MACRO TO TEST FOR I/O ERRORS
141                           .MACRO  TST1O$  SB
142                           .ENABL  LSB
143                           CMPB    SB,#IS.SUC  ;TEST FOR SUCCESSFUL I/O
144                           BEQ     1$
145                           MOV     SB,R0
146                           JSR     PC,IOERR    ;ABORT IF I/O WAS BAD
147  1$:                                          ;CONTINUE
148                           .DSABL  LSB
149                           .ENDM   TST1O$
150  ;
151  ;
152  URMFW:
153  ;READ IC.DAT, IS.DAT, & XLIST.DAT INTO CORE,
154                           LOAD$   #FDBIC,#ICBFSZ,#ICBUF
155  144156  012700  000000'          MOV     #FDBIC,R0    ;FILE DESCRIPTOR BLOCK ADR
     144162  012701  002070           MOV     #ICBFSZ,R1   ;SIZE (BYTES) OF DEST BUFFER
     144166  012702  134600'          MOV     #ICBUF,R2    ;STARTING ADR OF DESTINATION
     144172  004767  003254           JSR     PC,RDNWDS
156                           LOAD$   #FDBIS,#ISDFSZ,#ISBUF
     144176  012700  000176'          MOV     #FDBIS,R0    ;FILE DESCRIPTOR BLOCK ADR
     144202  012701  002070           MOV     #ISBFSZ,R1   ;SIZE (BYTES) OF DEST BUFFER
     144206  012702  136670'          MOV     #ISBUF,R2    ;STARTING ADR OF DESTINATION
     144212  004767  003234           JSR     PC,RDNWDS
159                           LOAD$   #FDBXL,#XLSTSZ,#XLBUF
     144216  012700  000374'          MOV     #FDBXL,R0    ;FILE DESCRIPTOR BLOCK ADR
     144222  012701  003000           MOV     #XLSTSZ,R1   ;SIZE (BYTES) OF DEST BUFFER
     144226  012702  140760'          MOV     #XLBUF,R2    ;STARTING ADR OF DESTINATION
     144232  004767  003214           JSR     PC,RDNWDS
```

```
                                    ;CALCULATE FACTOR FOR PRO-RATING RU VALUES
160  144236  016701          MOV    ALPHSH,R1
161  144242  016703          MOV    THRSH1,R3
162  144246  156703          SUB    THRSH2,R3
163  144252  016704          MOV    THRSH2,R4             ;T2-T1
164  144256  005005          CLR    R5
165  144262  005401          NEG    R1
166  144264  072301          ASHC   R1,R4
167  144266  071403          DIV    R3,R4                 ;(T2/(T2-T1))*2**(-ALPHSH)
168         010447          MOV    R4,ALPHA
169  144266
170                              ;SET UP TO DO FULL PROJECTION
171  144272  012767  040000' 003304    MOV   #GPBUF1,IGP
172  144300  012767  000001  003312    MOV   #1,ITHI
173  144306  012767  000055  003266    MOV   #NYGRPS,THGCNT
174  144314  016767          MOV    GOUTSS,GPSKG  003244  003414
175
176                              ;PREPARE TO CALCULATE 1 G-GROUP:
177
178  144322  012700  000000  CALCG:  MOV   #GPBSZ,R0
179  144326  012701  040000' MOV    #GPBUF1,R1
180  144332  005021          CLR    (R1)+
181  144334  077002          SOB    R0,CLRGLF
182  144336  012767  000020  003370  MOV   #NYGRPS,YGCNT
183  144344  012767  000400  003270  MOV   #NSPDIS,IYT
184         143760'          OPENGR MOV   #FDBING,...,ERR
     144352  000000G
             000000G
     144356  143760' MOV   NB,#FO.RD,         MOVB #FO.RD,F.FACC(R0)
     144364  112760  000767
     144364  004767  000000G JSR    PC,.OPEN
     144370  103002          BCC    .+6
     144372  064767  003152  JSR    PC,.ERR

185                              ;SKIP PAST 1ST 2 RECORDS OF 256 SECTOR FILE
186
187  144376  012704  000000' MOV    #FBUF,R4
188  144402                   READ$  #FDBING,R4,,,#3,#SB3,.ERR
     144402  012700  143760'  .IIF   NB,R4,   MOV    R4,F.DKDS+2(R0)
     144406  010460  000022   .IIF   NB,#3,   MOVB   #3,F.DKEF(R0)
     144412  112760  000003
     144420  012760  147730  .IIF   NB,#SB3,  MOV    #SB3,F.DKST(R0)
     144426  004767  000000G  JSR    PC,.READ
     144432  103003           BCC    .+6
     144434  004767  003110   JSR    PC,.ERR
189                              WAIT$  #FDBING,R0
     144440  012700  143760'  .IIF   NB,#3,   MOVB   #3,F.EFN(R0)
     144444  112760  000003
     144452  012760  147730  .IIF   NB,#SB3,  MOV    #SB3,F.DKST(R0)
     144460  004767  000000G  JSR    PC,.WAIT
                              TSTIO$ SB3
     144464  126727  003240   CMPB   SB3,#IS.SUC          ;TEST FOR SUCCESSFUL I/O
             001404           BEQ    10
190  144464  001404          
     144472  016700  003230   MOV    SB3,R0
     144474  004767  003054   JSR    PC,IOERR             ;ABORT IF I/O WAS BAD
191  144504  012704  000000'  MOV    #FBUF,R4
```

```
192  144510  012700  143760'                  READ3   MOV    #FDBIMG,R4
     144514  010460  000022                          .IIF          NB,R4,   MOV    R4,F.BKDS+2(R0)
     144520  112760  000003  147730'                 .IIF          NB,#3,   MOVB   #3,F.BKEF(R0)
     144526  012760  0000000G                        .IIF          NB,#SB3,  MOV           #SB3,F.BKST(R0)
     144534  004767  102002                          JSR    PC,.READ
     144540         004476                           BCC    .+6
     144542         3002                             JSR    PC,ERR
193  144546  012700  143760'                         MOV    #FDBIMG,R0
     144552  112760  000003  147730'                 .IIF          NB,#3,   MOVB   #3,F.EFN(R0)
     144560  012760  000003  147730'                 .IIF          NB,#SB3,  MOV           #SB3,F.BKST(R0)
     144566  004767  0000000G                        JSR    PC,.WAIT
194  144572  126727  003132                  TSTIO$  CMPB   SB3,#IS.SUC    ;TEST FOR SUCCESSFUL I/O
     144600  001404                                  BEQ    1$
     144602  016700  003122                          MOV    SB3,R0
     144606  004767  002746                          JSR    PC,IOERR       ;ABORT IF I/O WAS BAD
195  144612  012705  000020                  READFG: MOV    #NYS,R5        ;READ AN F-GROUP (Y-GROUP)
196  144616  012704  000000'                         MOV    #FBUF,R4
197  144622  012700  143760'                 READR$  MOV    #FDBIMG,R0
     144626  010460  000022                          .IIF          NB,R4,   MOV    R4,F.BKDS+2(R0)
     144632  112760  000003  147730'                 .IIF          NB,#3,   MOVB   #3,F.BKEF(R0)
     144640  012760  000003  147730'                 .IIF          NB,#SB3,  MOV           #SB3,F.BKST(R0)
     144646  004767  0000000G                        JSR    PC,.READ
     144652         103002                           BCC    .+6
     144654  004767  002670                          JSR    PC,ERR
198  144660  012700  143760'                         MOV    #FDBIMG,R0
     144664  112760  000003  147730'                 .IIF          NB,#3,   MOVB   #3,F.EFN(R0)
     144672  012760  000003  147730'                 .IIF          NB,#SB3,  MOV           #SB3,F.BKST(R0)
     144700  004767  0000000G                        JSR    PC,.WAIT
199  144704  126727  003020                  TSTIO$  CMPB   SB3,#IS.SUC    ;TEST FOR SUCCESSFUL I/O
     144712  001404                                  BEQ    1$
     144714  016700  003010                          MOV    SB3,R0
     144720  004767  002634                          JSR    PC,IOERR       ;ABORT IF I/O WAS BAD
200  144724  062704  001000                          ADD    #FBYTSC,R4
201  144730  077544                                  SOB    R5,READLP
202  144732  012701  040000                          MOV    #FBUFSZ,R1
203  144736  006201                                  ASR    R1
204  144740  006201                                  ASR    R1
205  144742  012703  040000'                         MOV    #FBUF+FBUFSZ,R3   ;OUTPUT POINTER
206  144746  012702  020000'                 EXPDLP: MOV    #FBUF+FBUFSZ/2+FBUF,R2  ;INPUT POINTER
207  144752  014243                                  MOV    -(R2),-(R3)
208  144754  005043                                  CLR    -(R3)
209  144756  077103                                  SOB    R1,EXPDLP
210
211  ;PROJECT EACH MU IN THE F GROUP INTO ALL PROJECTIONS:
212  144760  012701  000400                  PROCFG: MOV    #NSPDIS,R1
213  144764  166701  002652                          SUB    IYT,R1
214  144770  070127  000006                          MUL    #6,R1
```

```
215 144774 162701 143760'         ADD    #XLBUF,R1           ;POINT TO APPROP PART OF XLIST
216 145000 010167 002736          MOV    R1,XLVEC
217
218 145004 004767 000334          JSR    PC,PROJEC           ;CALL PROJEC(IGP,ITH1,IYT,XLVEC)
219
220 145010 162767 000020 002624   SUB    #NYS,IYT
221 145016 005367 002712          DEC    YCCNT               ;ARE THERE MORE F-GROUPS IN IMAGE?
222 145022 003273                 BGT    READFG              ;BRANCH IF THERE ARE
223
224 145024 012700 143760'         CLOSE$ #FDBIGG,ERR         ;ELSE CLEANUP & WRITE THE PROJECTIONS
                                  MOV    #FDBIMG,R0
    145030 004767 0000000G        JSR    PC,.CLOSE
    145034 103002                 BCC    .+6
                                  JSR    PC,ERR
225 145036 004767 000505          JSR    PC,ERR
226 145042 012703 040000'         MOV    #GPBUF1,R3
227 145046 012702 070000'         MOV    #GPBUF2,R2
      145052 012701 014000        MOV    #GPBISZ/2,R1
NORMLP: 
    145056 012204                 MOV    (R2)+,R4
    145060 011305                 MOV    (R3),R5
    145062 075467 002630          ASHC   GSHIFT,R4
    145066 070467 002476          MUL    GFACT,R4
    145072 010423                 MOV    R4,(R3)+
    145074 077110                 SOB    R1,NORMLP           ;SAVE SINGLE PREC NORMALIZED RESULT

;FILTER OUT THE 256 CYCLE RIPPLE:

PREFLP:
236 145076 012705 000014          MOV    #NTHPTS,R5
237 145102 012703 040000'         MOV    #GPBUF1,R2
238 145106 011200                 MOV    (R2),R0
239 145110 060000                 ADD    R0,R0
240 145112 066200 006002          ADD    2(R2),R0
241 145116 010062 030000          MOV    R0,(R2),R0
242 145122 062702 000002          MOV    R0,GPBISZ(R2)
243 145126 012701 000776          ADD    #2,R2
244 145132 016200 177776          MOV    #NSPSAM-1,R1
FILTLP:                           MOV    -2(R2),R0
245 145136 061200                 ADD    (R2),R0
246 145140 066200 000002          ADD    (R2),R0
247 145142 066200 030000          ADD    2(R2),R0
248 145146 010962 062702          MOV    R0,GPBISZ(R2)
249 145152 062702 000002          ADD    #2,R2
250 145156 077113                 SOB    R1,FILTLP
251 145160 062702 000002          ADD    #2,R2
252 145164 077530                 SOB    R5,PREFLP           ;COMPLETE 3-POINT SMOOTHING
                                                             ;SAVE NTH POINT
253
QIO#S:
254 145166 005046                 CLR    #10,WLB,#DK1,#1,,#SB1,,#GPBUF2,#GPBISZ,#0,GPSEC,ERR
    145170 016746 002542          MOV    GPSEC,-(SP)
    145174 005046                 CLR    -(SP)
    145176 005046                 CLR    -(SP)
    145200 012746 030000          MOV    #GPBUF2,-(SP)
    145204 012746 070000'         MOV    #GPBISZ,-(SP)
    145210 005046                 CLR    -(SP)
    145212 012746 147720'         MOV    #SB1,-(SP)
    145216 005046                 CLR    -(SP)
```

```
145220  112716  000001                    MOVB    #1,(SP)
145224  012746  000002                    MOV     #DK1,-(SP)
145230  012746  000000G                   MOV     #10.WLE,-(SP)
145234  012746  014                       MOV     (PC)+,-(SP)
145240  001                               .BYTE   1,12.
145242  104377                            EMT     ^O<377>
145244  103002                            BCC     .+6
145246  004767  002300                    JSR     PC,ERR
145250                                    VTSEBS
255
145250  012746  000001                    MOV     #1,-(SP)
145254  012746  002                       MOV     (PC)+,-(SP)
145260  051                               .BYTE   41.,2
145262  104377                            EMT     ^O<377>
256
145262  126727  002432 000000G            TSTIOS
145270  001404                             CMPB    SB1,#IS.SUC        ;TEST FOR SUCCESSFUL I/O
145272  016700  002422                     BEQ     10
145276  004767  002256                     MOV     SB1,R0
                                           JSR     PC,10ERR           ;ABORT IF I/O WAS BAD 257
258  145302  052767  000030  002426       ADD     #2*NTHETS,GPSEC    ;SET UP FOR NEXT THETA GROUP
259  145310  052767  000014  002302       ADD     #NTHETS,ITHI       ;ARE THERE MORE TO CALCULATE?
260  145316  005367  002260               DEC     THSCNT             ;RETURN IF THERE ARE
261  145322  003402                        BLE     TERM
262  145324  000167  176772                JMP     CALCG 263
264  ;ALL DONE!
265  TERM:   EXITGS
145330  012746                             MOV     (PC)+,-(SP)
145332  063                                .BYTE   51.,1
145334  104377                             EMT     ^O<377>            ;THE END !

266
267            EXITGS
145336  012746                             MOV     (PC)+,-(SP)
145340  063                                .BYTE   51.,1
145342  104377                             EMT     ^O<377>

268  ;PROJECTION SUBROUTINE (USES IGP,ITHI,IYT,XLVEC)
269  PROJEC: MOV     ITHI,R0
270  145344  016700  002250               DEC     R0
271  145350  005300                        ASL     R0
272  145352  006300                        ASL     R0
273  145354  010001                        MOV     R0,R1
274  145356  066700  002240               ADD     R0,COSORG          ;INIT ADR OF COS VALUES TO USE.
275  145362  010067  002240               MOV     IS,R1
276  145366  066701                        ADD     R1,SINORG          ;INIT ADR OF SIN VALUES TO USE
277  145372  010167  002232               MOV     XLVEC,XLPTR        ;INIT ADR OF XLIST VALUES TO USE
278  145376  016767  002340               MOV 279
280  ;COMPUTE MATRIX OF X*COS(THETA) VALUES (NTHE X NSPDSP)
281  145404  016767  002216  002220       MOV     COSORG,ICPTR       ;INITIALIZE IC POINTER FOR ITHI
282  145412  005067  002216               CLR     THEREL             ;THETA (RELATIVE)
283  145416  010667  002222               MOV     SP,SAVSTK          ;SAVE STACK POINTER
284  145422  016706  002162               MOV     NTHE,SP
285  145426  006306                        ASL     SP                 ;BYTES PER ROW OF XCBUF
```

```
286  145430  010667              MOV   SP,TWONTH
287  145434  017700              MOV   @ICPTR,R0
288                          ;ROW (OVERALL)
289  145440  062767  002246  LOOP:
                             ADD   #2,ICPTR       ;GET 1ST VALUE OF COSINE
290  145446  016701  002172      MOV   NSPDSP,R1   ;SET POINTER FOR NEXT THETA
291  145452  006201  000002      ASR   R1          ;SET X COUNTER
292  145454  010903              MOV   R0,R3
293  145456  005403              NEG   R3
294  145460  006702              SXT   R2          ;1ST X = -1 + DELTA X,
295  145462  006300              ASL   R3
296  145464  016704  002144      MOV   THFREL,R4   ;DELTA X = 2
297  145470  006304              ASL   R4          ;INITIALIZE UP & DOWN VECTORS:
298  145472  062704  120000      ADD   #XCRUF,R4   ;POINT TO TOP OF COLUMN
299  145476  016705  002112      MOV   NSPDSP,R5
300  145502  070567  002102      MUL   NTHF,R5
301  145506  060405              ADD   R4,R5
302  145510  010567  002122      MOV   R5,XCPPTR   ;POINTER FOR POSITIVE X VALUES
303  145514  160505              SUB   SP,R5
304  145516  010567  002116      MOV   R5,XCMPTR   ;POINTER FOR NEGATIVE X VALUES
305                          ;COLUMN LOOP:
306  145522  005700          XCULP: TST   R0
307  145524  006705              SXT   R5
308  145526  060003              ADD   R0,R3
309  145530  005505              ADC   R5
310  145532  060502              ADD   R5,R2
311  145534  010204              MOV   R2,R4
312  145536  010305              MOV   R3,R5
313  145540  073427              ASHC  #5,R4
314  145544  005505              ASL   R5
315  145546  010477              ADC   R4
316  145550  010477  002062      MOV   R4,@XCPPTR
317  145554  005404              NEG   R4
318  145556  010477  002056      MOV   R4,@XCMPTR
319  145562  160667  002044      SUB   SP,XCPPTR
320  145566  060667              ADD   SP,XCPPTR
321  145572  077125              SOB   R1,XCULP
322
323  145574  017700  002032      MOV   @ICPTR,R0
324  145600  005267  002030      INC   THEREL
325  145604  026767  002024      CMP   THEREL,NTHE
326  145612  002712  001776      BLT   XCRLP
327
328  145614  016700  002022      MOV   IYT,R0      ;GET NEXT COS
329  145620  006300              ASL   R0
330  145622  166700  001766      SUB   NSPDSP,R0
331  145626  005300              DEC   R0
332  145630  010067  002016      MOV   R0,YTOP
333
334
335  145634  016700  001746      MOV   NSPSNP,R0
336  145640  005300              DEC   R0
337  145642  066700  001736      ADD   ICP,R0      ;YTOP=-NSPDSP-1+2*IYT
338  145646  010067  002004      MOV   R0,ADCTRL   ;ICP+2(NSPSMT-1)/2
339                                                ;ADR OF CENTER OF 1ST G' IN CORE
```

```
                                ;COMPUTE MATRIX OF Y*SIN(THETA)+CENTER ADDRESS CONSTANTS (YSBUF)
340  145652  016767  001752  002014         MOV   SINORG,ISPTR
341  145660  016767  001724  002026         MOV   NTHE,THECNT
342  145666  016706               016       MOV   TWONTH,SP
343  145672  012767  134000' 002010         MOV   #YSBUF,YSCOLA
344  145700  016767  001752  001770         MOV   ADCTR1,ADCTRN
345  145706  017701                         MOV   @ISPTR,R1
346  145712  006700                         SXT   R0
347  145714  062767  000002  001752  YSRLP: ADD   #2,ISPTR
348  145722  010102                         MOV   R1,R2
349  145724  006301                         ASL   R1
350  145726  070267  001720                 MUL   YTOP,R2
351  145732  016767  001660  001746         MOV   NY,YCOUNT
352  145740  016767  001752  001744         MOV   YSCOLA,YSPTR
353  145746  010204                         MOV   R2,R4
354  145750  010305                         MOV   R3,R5
355  145752  073427  000005          YSCLP: ASHC  #5,R4
356  145756  006305                         ASL   R5
357  145760  005504                         ADC   R4
358  145762  056704  001710                 ADD   ADCTRN,R4
359  145766  010477  001726                 MOV   R4,@YSPTR
360  145772  060667  001714                 ADD   SP,YSPTR
361  145776  150103                         MOV   R1,R3
362  146000  055602                         SBC   R2
363  146002  160902                         SUB   R0,R2
364  146004  005367  001676                 DEC   YCOUNT
365  146010  003356                         BCT   YSCLP
366
367                              ;GET READY FOR NEXT COLUMN (THETA) OF YSBUF:
368  146012  066767  001646  001656         ADD   GETSR,ADCTRN
369  146020  062767  000002  001670         ADD   #2,YSCOLA
370  146026  005367  001662                 DEC   THECNT
371  146032  003325                         BGT   YSILP
372
373
374
375  146034  016767  001556  001644         MOV   NY,YCOUNT
376  146042  012767  134000' 001640         MOV   #YSBUF,YSROAD
377
378                              ;PROJECTION LOOP
379  146050  016767  001670  001604  YLP:   MOV   @XLPTR,FXYADR
380  146056  016700                         MOV   FXYADR,R0
381  146062  062700  000002                 ADD   #2,R0
382  146066  010067                         MOV   R0,FXYAP2
383  146072  062767  000002  001644         ADD   #2,XLPTR
384  146100  017767  001640  001576         MOV   @XLPTR,XCOUNT
385  146106  062767  000002  001630         ADD   #2,XLPTR
386  146114  017700                         MOV   @XLPTR,R0
387  146120  062767  000002  001616         ADD   #2,XLPTR
388  146126  016701                         MOV   YSROAD,R1
389  146132  017705                  XLP:   MOV   @FXYAP2,R5
390  146136  020567  001532                 CMP   R5,THRSH1
391  146142  003092                         BGT   TRY2
392  146144  000167  000042                 JMP   USER5
```

| | | | | | |
|---|---|---|---|---|---|
| 393 | 146150 | 020567 | 001420 | TRYT2: | CMP R5,THRSH2 | ;NU > THRSH2? |
| 394 | 146154 | 002403 | | | BLT ADJNU | ;NO. DISTRIBUTE BETWEEN BONE AND S.T. |
| 395 | 146156 | 005005 | | | CLR R5 | ;YES. IGNORE IT (PURE BONE) |
| 396 | 146160 | 000167 | 000026 | | JMP USER5 | ;GO THROUGH THE MOTIONS FOR POINTERS |
| 397 | 146164 | 166705 | 001402 | ADJNU: | SUB THRSH1,R5 | ;NU-THRSH1 |
| 398 | 146170 | 016504 | | | MOV R5,R4 | |
| 399 | 146172 | 070467 | 001402 | | MUL ALPHA,R4 | |
| 400 | 146176 | 073467 | 001374 | | ASHC ALPHSH,R4 | ;*ALPHA |
| 401 | 146202 | 010405 | | | MOV R4,R5 | |
| 402 | 146204 | 167705 | 001460 | | SUB @FXYAP2,R5 | |
| 403 | 146210 | 005405 | | | NEG R5 | |
| 404 | 146212 | 010505 | | | MOV R5,R5 | |
| 405 | 146214 | 006704 | | | SXT R4 | |
| 406 | | | | USER5: | | |
| 407 | 146216 | 000014 | | ;INNER DOTHTS: | LSB | |
| 408 | | | | | .REPT NTHETS | |
| 409 | | | | | .ENABL LSB | |
| 410 | | | | | MOV (R0)+,R2 | ;GET X*COS |
| 411 | | | | | ADD (R1)+,R2 | ;ADD Y*SIN + CENTER ADDRESS |
| 412 | | | | | ROR R2 | |
| 413 | | | | | BCS 1$ | ;BRANCH IF ADDRESS IS BORDERLINE |
| 414 | | | | | ASL R2 | ;POINT TO LEAST SIG 16 BITS OF G |
| 415 | | | | | ADD R2,R2 | ;DO DBL PREC ADD TO 1 POINT |
| 416 | | | | | ADD R5,(R2) | |
| 417 | | | | | ADC GPBISZ(R2) | |
| 418 | | | | | ADD R4,GPBISZ(R2) | |
| 419 | | | | | BR 2$ | ;REJOIN MAINSTREAM |
| 420 | | | | 1$: | ASR R5 | ;TEMPORARILY SCALE NU TO NU/2 |
| 421 | | | | | ASL R2 | |
| 422 | | | | | ADD R5,(R2) | |
| 423 | | | | | ADC GPBISZ(R2) | |
| 424 | | | | | ADD R4,GPBISZ(R2) | ;CONTRIBUTE NU/2 TO 2 POINTS |
| 425 | | | | | ADD #2,R2 | |
| 426 | | | | | ADD R5,(R2) | |
| 427 | | | | | ADC GPBISZ(R2) | |
| 428 | | | | | ADD R4,GPBISZ(R2) | |
| 429 | | | | | ASL R5 | ;RESTORE NU TO ORIG SCALING |
| 430 | | | | 2$: | .DSABL LSB | |
| | | | | | .ENDM | |
| 431 | 146216 | 012002 | | | MOV (R0)+,R2 | ;GET X*COS |
| 432 | 146220 | 062102 | | | ADD (R1)+,R2 | ;ADD Y*SIN + CENTER ADDRESS |
| 433 | 146222 | 006002 | | | ROR R2 | |
| 434 | 146224 | 103407 | | | BCS 1$ | ;BRANCH IF ADDRESS IS BORDERLINE |
| 435 | 146226 | 006302 | | | ASL R2 | ;POINT TO LEAST SIG 16 BITS OF G |
| 436 | 146230 | 060202 | | | ADD R2,R2 | ;DO DBL PREC ADD TO 1 POINT |
| 437 | 146232 | 005512 | | | ADD R5,(R2) | |
| 438 | 146234 | 005562 030000 | | | ADC GPBISZ(R2) | |
| 439 | 146236 | 060462 030000 | | | ADD R4,GPBISZ(R2) | |
| 440 | 146242 | 000417 | | | BR 2$ | ;REJOIN MAINSTREAM |
| 441 | 146244 | 006205 | | 1$: | ASR R5 | ;TEMPORARILY SCALE NU TO NU/2 |
| 442 | 146246 | 006302 | | | ASL R2 | |
| 443 | 146250 | 060512 | | | ADD R5,(R2) | |
| 444 | 146252 | 005562 030000 | | | ADC GPBISZ(R2) | |
| 445 | 146256 | 060462 030000 | | | ADD R4,GPBISZ(R2) | |
| 446 | 146262 | 062702 000002 | | | ADD #2,R2 | ;CONTRIBUTE NU/2 TO 2 POINTS |
| 447 | 146266 | 060512 | | | ADD R5,(R2) | |

| Address | Code | | Op | Operands | Comment |
|---|---|---|---|---|---|
| 146270 | 005562 | 030000 | ADC | GPB1SZ(R2) | |
| 146274 | 060462 | | ADD | R4,GPB1SZ(R2) | ;RESTORE MU TO ORIG SCALING |
| 146300 | 006305 | | ASL | R5 | ;GET X*COS |
| 146302 | 012002 | | MOV | (R0)+,R2 | |
| 146304 | 062102 | | ADD | (R1)+,R2 | ;ADD Y*SIN + CENTER ADDRESS |
| 146306 | 066002 | | ROR | R2 | |
| 146310 | 103407 | | BCS | 1$ | ;BRANCH IF ADDRESS IS BORDERLINE |
| 146312 | 006302 | | ASL | R2 | ;POINT TO LEAST SIG 16 BITS OF G |
| 146314 | 060512 | | ADD | R5,(R2) | ;DO DBL PREC ADD TO 1 POINT |
| 146316 | 005562 | 030000 | ADC | GPB1SZ(R2) | |
| 146322 | 060462 | 030000 | ADD | R4,GPB1SZ(R2) | |
| 146326 | 000417 | | BR | 2$ | ;REJOIN MAINSTREAM |
| 146330 | 006205 | | ASR | R5 | ;TEMPORARILY SCALE MU TO MU/2 |
| 146332 | 006302 | | ASL | R2 | |
| 146334 | 060512 | | ADD | R5,(R2) | ;CONTRIBUTE MU/2 TO 2 POINTS |
| 146336 | 005562 | 030000 | ADC | GPB1SZ(R2) | |
| 146342 | 060462 | 030000 | ADD | R4,GPB1SZ(R2) | |
| 146346 | 062702 | 000002 | ADD | #2,R2 | |
| 146352 | 060512 | | ADD | R5,(R2) | |
| 146354 | 005562 | 030000 | ADC | GPB1SZ(R2) | |
| 146360 | 060462 | 030000 | ADD | R4,GPB1SZ(R2) | |
| 146364 | 006305 | | ASL | R5 | ;RESTORE MU TO ORIG SCALING |
| 146366 | 012002 | | MOV | (R0)+,R2 | ;GET X*COS |
| 146370 | 062102 | | ADD | (R1)+,R2 | ;ADD Y*SIN + CENTER ADDRESS |
| 146372 | 066002 | | ROR | R2 | |
| 146374 | 103407 | | BCS | 1$ | ;BRANCH IF ADDRESS IS BORDERLINE |
| 146376 | 006302 | | ASL | R2 | ;POINT TO LEAST SIG 16 BITS OF G |
| 146400 | 060512 | | ADD | R5,(R2) | ;DO DBL PREC ADD TO 1 POINT |
| 146402 | 005562 | 030000 | ADC | GPB1SZ(R2) | |
| 146406 | 060462 | 030000 | ADD | R4,GPB1SZ(R2) | |
| 146412 | 000417 | | BR | 2$ | ;REJOIN MAINSTREAM |
| 146414 | 006205 | | ASR | R5 | ;TEMPORARILY SCALE MU TO MU/2 |
| 146416 | 006302 | | ASL | R2 | |
| 146420 | 060512 | | ADD | R5,(R2) | ;CONTRIBUTE MU/2 TO 2 POINTS |
| 146422 | 005562 | 030000 | ADC | GPB1SZ(R2) | |
| 146426 | 060462 | 030000 | ADD | R4,GPB1SZ(R2) | |
| 146432 | 062702 | 000002 | ADD | #2,R2 | |
| 146436 | 060512 | | ADD | R5,(R2) | |
| 146440 | 005562 | 030000 | ADC | GPB1SZ(R2) | |
| 146444 | 060462 | 030000 | ADD | R4,GPB1SZ(R2) | |
| 146450 | 006305 | | ASL | R5 | ;RESTORE MU TO ORIG SCALING |
| 146452 | 012002 | | MOV | (R0)+,R2 | ;GET X*COS |
| 146454 | 062102 | | ADD | (R1)+,R2 | ;ADD Y*SIN + CENTER ADDRESS |
| 146456 | 066002 | | ROR | R2 | |
| 146460 | 103407 | | BCS | 1$ | ;BRANCH IF ADDRESS IS BORDERLINE |
| 146462 | 006302 | | ASL | R2 | ;POINT TO LEAST SIG 16 BITS OF G |
| 146464 | 060512 | | ADD | R5,(R2) | ;DO DBL PREC ADD TO 1 POINT |
| 146466 | 005562 | 030000 | ADC | GPB1SZ(R2) | |
| 146472 | 060462 | 030000 | ADD | R4,GPB1SZ(R2) | |
| 146476 | 000417 | | BR | 2$ | ;REJOIN MAINSTREAM |
| 146500 | 006205 | | ASR | R5 | ;TEMPORARILY SCALE MU TO MU/2 |
| 146502 | 006302 | | ASL | R2 | |
| 146504 | 060512 | | ADD | R5,(R2) | ;CONTRIBUTE MU/2 TO 2 POINTS |
| 146506 | 005562 | 030000 | ADC | GPB1SZ(R2) | |

```
146512  060462  030000          ADD    R4,GPB1SZ(R2)
146516  062702  000002          ADD    #2,R2
146522  060512                  ADD    R5,(R2)
146524  060562  030000          ADD    GPB1SZ(R2)
146530  060462  030000          ADD    R4,GPB1SZ(R2)
146534  006305                  ASL    R5           ;RESTORE MU TO ORIG SCALING
146536  012002                  MOV    (R0)+,R2     ;GET X*COS
146540  062102                  ADD    (R1)+,R2     ;ADD Y*SIN + CENTER ADDRESS
146542  006002                  ROR    R2
146544  103407                  BCS    1$           ;BRANCH IF ADDRESS IS BORDERLINE
146546  006302                  ASL    R2           ;POINT TO LEAST SIG 16 BITS OF G
146550  060512                  ADD    R5,(R2)      ;DO DBL PREC ADD TO 1 POINT
146552  005562  030000          ADC    GPB1SZ(R2)
146556  060462  030000          ADD    R4,GPB1SZ(R2)
146562  000417                  BR     2$           ;REJOIN MAINSTREAM
146564  006305                  ASR    R5           ;TEMPORARILY SCALE MU TO MU/2
146566  006302          1$:     ASL    R2
146570  060512                  ADD    R5,(R2)      ;CONTRIBUTE MU/2 TO 2 POINTS
146572  005562  030000          ADC    GPB1SZ(R2)
146576  060462  030000          ADD    R4,GPB1SZ(R2)
146602  062702  000002          ADD    #2,R2
146606  060512                  ADD    R5,(R2)
146610  005562  030000          ADC    GPB1SZ(R2)
146614  060462  030000          ADD    R4,GPB1SZ(R2)
146620  006305                  ASR    R5           ;RESTORE MU TO ORIG SCALING
146622  012002                  MOV    (R0)+,R2     ;GET X*COS
146624  062102                  ADD    (R1)+,R2     ;ADD Y*SIN + CENTER ADDRESS
146626  006002                  ROR    R2
146630  103407                  BCS    1$           ;BRANCH IF ADDRESS IS BORDERLINE
146632  006302                  ASL    R2           ;POINT TO LEAST SIG 16 BITS OF G
146634  060512                  ADD    R5,(R2)      ;DO DBL PREC ADD TO 1 POINT
146636  005562  030000          ADC    GPB1SZ(R2)
146642  060462  030000          ADD    R4,GPB1SZ(R2)
146646  000417                  BR     2$           ;REJOIN MAINSTREAM
146650  006205                  ASR    R5           ;TEMPORARILY SCALE MU TO MU/2
146652  006302          1$:     ASL    R2
146654  060512                  ADD    R5,(R2)      ;CONTRIBUTE MU/2 TO 2 POINTS
146656  005562  030000          ADC    GPB1SZ(R2)
146662  060462  030000          ADD    R4,GPB1SZ(R2)
146666  062702  000002          ADD    #2,R2
146672  060512                  ADD    R5,(R2)
146674  005562  030000          ADC    GPB1SZ(R2)
146700  060462  030000          ADD    R4,GPB1SZ(R2)
146704  006305                  ASL    R5           ;RESTORE MU TO ORIG SCALING
146706  012002                  MOV    (R0)+,R2     ;GET X*COS
146710  062102                  ADD    (R1)+,R2     ;ADD Y*SIN + CENTER ADDRESS
146712  006002                  ROR    R2
146714  103407                  BCS    1$           ;BRANCH IF ADDRESS IS BORDERLINE
146716  006302                  ASL    R2           ;POINT TO LEAST SIG 16 BITS OF G
146720  060512                  ADD    R5,(R2)      ;DO DBL PREC ADD TO 1 POINT
146722  005562  030000          ADC    GPB1SZ(R2)
146726  060462  030000          ADD    R4,GPB1SZ(R2)
146732  000417                  BR     2$           ;REJOIN MAINSTREAM
146734  006205          1$:     ASR    R5           ;TEMPORARILY SCALE MU TO MU/2
```

```
146736  006392           ASL  R2                      ;CONTRIBUTE MU/2 TO 2 POINTS
146740  060512           ADD  R5,(R2)
146746  005562           ADD  GPB1SZ(R2)
146752  060462           ADD  R4,GPB1SZ(R2)
146756  062702  030000   ADD  #2,R2
146760  060512           ADD  R5,(R2)
146764  005562           ADD  GPB1SZ(R2)
146770  060462           ADD  R4,GPB1SZ(R2)
146774  006305           ASL  R5                      ;RESTORE MU TO ORIG SCALING
146776  012002           MOV  (R0)+,R2                ;GET X*COS
147000  063102           ADD  (R1)+,R2                ;ADD Y*SIN + CENTER ADDRESS
147002  060002           ADD  R2                      
147004  103407           BCS  13                      ;BRANCH IF ADDRESS IS BORDERLINE
147006  006302           ASL  R2                      ;POINT TO LEAST SIG 16 BITS OF (
147010  005562           ADD  GPB1SZ(R2)              ;DO DBL PREC ADD TO 1 POINT
147012  060462  030000   ADD  R4,GPB1SZ(R2)
147016  000417           BR   23                      ;REJOIN MAINSTREAM
147020  006205           ASR  R5                      ;TEMPORARILY SCALE MU TO MU/2
147022  006302           ASL  R2
147024  060512           ADD  R5,(R2)                 ;CONTRIBUTE MU/2 TO 2 POINTS
147026  005562           ADD  GPB1SZ(R2)
147032  060462           ADD  R4,GPB1SZ(R2)
147036  062702  030000   ADD  #2,R2
147042  060512           ADD  R5,(R2)
147044  005562           ADD  GPB1SZ(R2)
147050  060462           ADD  R4,GPB1SZ(R2)
147054  006305           ASL  R5                      ;RESTORE MU TO ORIG SCALING
147056  012002           MOV  (R0)+,R2                ;GET X*COS
147060  063102           ADD  (R1)+,R2                ;ADD Y*SIN + CENTER ADDRESS
147062  060002           ADD  R2
147064  103407           BCS  13                      ;BRANCH IF ADDRESS IS BORDERLINE
147066  006302           ASL  R2                      ;POINT TO LEAST SIG 16 BITS OF C
147070  005562           ADD  GPB1SZ(R2)              ;DO DBL PREC ADD TO 1 POINT
147072  060462  030000   ADD  R4,GPB1SZ(R2)
147076  000417           BR   23                      ;REJOIN MAINSTREAM
147102  006205           ASR  R5                      ;TEMPORARILY SCALE MU TO MU/2
147104  006302           ASL  R2
147106  060512           ADD  R5,(R2)                 ;CONTRIBUTE MU/2 TO 2 POINTS
147110  005562           ADD  GPB1SZ(R2)
147112  060462           ADD  R4,GPB1SZ(R2)
147116  062702  030000   ADD  #2,R2
147122  060512           ADD  R5,(R2)
147126  005562           ADD  GPB1SZ(R2)
147130  060462           ADD  R4,GPB1SZ(R2)
147134  006305           ASL  R5                      ;RESTORE MU TO ORIG SCALING
147136  012002           MOV  (R0)+,R2                ;GET X*COS
147142  063102           ADD  (R1)+,R2                ;ADD Y*SIN + CENTER ADDRESS
147144  060002           ADD  R2
147146  103407           BCS  13                      ;BRANCH IF ADDRESS IS BORDERLINE
147150  006302           ASL  R2                      ;POINT TO LEAST SIG 16 BITS OF C
147154  005562           ADD  GPB1SZ(R2)              ;DO DBL PREC ADD TO 1 POINT
147156  005562           ADD  GPB1SZ(R2)
```

```
147162  060462            ADD   R4,GPDISZ(R2)      ;REJOIN MAINSTREAM
147166  000417            BR    29                 ;TEMPORARILY SCALE NU TO NU/2
147170  006205            ASR   R5
147172  006302            ASL   R2
147174  060512            ADD   R5,(R2)            ;CONTRIBUTE NU/2 TO 2 POINTS
147176  005562            ADC   GPDISZ(R2)
147202  060462            ADD   R4,GPDISZ(R2)
147206  062702            ADD   #2,R2
147212  060512            ADD   R5,(R2)
147214  005562            ADC   GPDISZ(R2)
147220  060462            ADD   R4,GPDISZ(R2)
147224  006305            ASL   R5                 ;RESTORE NU TO ORIG SCALING
147226  012092            MOV   (R0)+,R2           ;GET X*COS
147230  062102            ADD   (R1)+,R2           ;ADD Y*SIN + CENTER ADDRESS
147232  006002            ROR   R2
147234  103407            BCS   15                 ;BRANCH IF ADDRESS IS BORDERLINE
147236  006302            ASL   R2                 ;POINT TO LEAST SIG 16 BITS OF C
147242  060512            ADD   R5,(R2)            ;DO DBL PREC ADD TO 1 POINT
147246  005562            ADC   GPDISZ(R2)
147252  060462            ADD   R4,GPDISZ(R2)
147254  000417            BR    29                 ;REJOIN MAINSTREAM
147256  006205            ASR   R5                 ;TEMPORARILY SCALE NU TO NU/2
147260  006302            ASL   R2
147262  060512            ADD   R5,(R2)            ;CONTRIBUTE NU/2 TO 2 POINTS
147266  005562            ADC   GPDISZ(R2)
147270  060462            ADD   R4,GPDISZ(R2)
147272  062702            ADD   #2,R2
147276  060512            ADD   R5,(R2)
147300  005562            ADC   GPDISZ(R2)
147304  060462            ADD   R4,GPDISZ(R2)
147310  000417            BR    29                 ;RESTORE NU TO ORIG SCALING
147312  006305            ASL   R5                 ;GET X*COS
147314  012002            MOV   (R0)+,R2           ;ADD Y*SIN + CENTER ADDRESS
147316  062102            ADD   (R1)+,R2
147320  006002            ROR   R2
147322  103407            BCS   15                 ;BRANCH IF ADDRESS IS BORDERLINE
147324  006302            ASL   R2                 ;POINT TO LEAST SIG 16 BITS OF C
147330  060512            ADD   R5,(R2)            ;DO DBL PREC ADD TO 1 POINT
147332  005562            ADC   GPDISZ(R2)
147336  060462            ADD   R4,GPDISZ(R2)
147340  000417            BR    29                 ;REJOIN MAINSTREAM
147342  006205            ASR   R5                 ;TEMPORARILY SCALE NU TO NU/2
147344  006302            ASL   R2
147346  060512            ADD   R5,(R2)            ;CONTRIBUTE NU/2 TO 2 POINTS
147352  005562            ADC   GPDISZ(R2)
147356  060462            ADD   R4,GPDISZ(R2)
147360  062702            ADD   #2,R2
147362  060512            ADD   R5,(R2)
147364  005562            ADC   GPDISZ(R2)
147370  060462            ADD   R4,GPDISZ(R2)
147374  006305            ASL   R5                 ;RESTORE NU TO ORIG SCALING 431
432
433
434  147376  062707  000256   ADD  #4,FXYADR
435  147404  062707  000256   ADD  #4,FXYAP2      ;GET SET FOR NEXT IN-CORE F(X,Y)
```

```
436  147412  005367  000266              DEC   XCOUNT                ;RELOOP FOR NEXT X,SAME Y
437  147416  003302                       BLE   BUMPY
438  147420  030167  176502              JMP   XLP
439  147424  066767  002252  000256      ADD   TWONTH,YSTROAD        ;ADVANCE Y ROW STARTING ADDRESS
440  147432  005367  000250              DEC   YCOUNT
441  147436  003402                       BLE   FBLKDN
442  147440  000167  176404              JMP   YLP                   ;START NEXT (LOWER) Y ROW
443
444
445  147444  016706  000174      FBLKDN: MOV   SAVSTK,SP             ;RESTORE STACK POINTER
446  147450  000207                       RTS   PC                    ;RETURN TO CALLER
447
448
449
450  ;SUBROUTINE TO LOAD A BUFFER WITH CONSTANTS FROM DISK
451  ;RDNWDS: OPEN@R R0,.,.,ERR
452  147452  112760  000000G  000043             .IIF        MOVB #FO.RD,F.FACC(R0)
     147460  000000G
     147464  103002                       JSR   N3,#FO.RD,
     147466  004767                       BCC   PC,.OPEN
                                          .+6
                                          JSR   PC,ERR
453  147472  004767  000000G      GETLP: GET@S R0,.,.,GETSQ
     147476  103002                       JSR   PC,,GETSQ
     147500  004767  000044               BCC   .+6
                                          JSR   PC,ERR
     ;COPY DATA WORDS READ INTO TARGET BUFFER
454  147504  012704  000574'              MOV   #RECBUF+2,R4          ;WHERE THE DATA STARTS
455  147510  016063  000024               MOV   F.NRBD(R0),R3         ;# OF BYTES JUST READ
456  147514  005303                       DEC   R3
457  147516  005303                       DEC   R3                    ;IGNORE 1ST WORD (FCS*8)
458  147520  160301                       SUB   R3,R1                 ;# OF DATA BYTES YET TO READ
459  147522  006203                       ASR   R3                    ;# OF WORDS TO COPY TO DEST BUFF
460  147524  012423              CTCPLP: MOV   (R4)+,(R2)+            ;COPY FROM RECBUF TO DEST BUFFER
461  147526  077302                       SOB   R3,CTCPLP
462  147530  005701                       TST   R1
463  147532  003357                       BGT   GETLP
                                          CLOSE@
464  147534  004767  000000G               JSR  PC,.CLOSE
465  147540  103002                        BCC  .+6
     147542  004767  000000G               JSR  PC,ERR
     147546  000207                        RTS  PC
466
467
468  147550  016700  000000G       ERR:  MOV   $DSW,R0
469  147554  012601                        MOV  (SP)+,R1
470  147556  000000                        HALT
471
472  147560  012601              IOERR:  MOV   (SP)+,R1
473  147562  000000                        HALT
474
475
476  147564  006300              COUTSS: .WORD  CWSSEC
477  147566  000015              CSHIFT: .WORD  15
478  147570  060000              GFACT:  .WORD  60000
479  147572  002300              THRSH1: .WORD  1216.     ;1ST THRESHHOLD (ABSOLUTE HOUNDSFIELDS)
```

| | | | | | | |
|---|---|---|---|---|---|---|
| 480 | 147574 | 005000 | | THRSH2: | .WORD | 1536. | ;2ND THRESHOLD
| 481 | 147576 | 000004 | | ALPUSH: | .WORD | 4 | ;SHIFT COUNT FOR SCALED MU CONTRIBUTIONS
| 482 | 147600 | 000000 | | ALPHA: | .WORD | 0 | ;COMPUTED BY PROGRAM. T2/(T2-T1) *2**16-ALPUSH
| 483 | | | | | | |
| 484 | 147602 | 000000 | | THGCNT: | .WORD | 0 |
| 485 | 147604 | 000000 | | IGP: | .WORD | 0 |
| 486 | 147606 | 000777 | | NSPSMP: | .WORD | NSTSAM |
| 487 | 147610 | 000014 | | NTHE: | .WORD | NTHETS |
| 488 | 147612 | 000014 | | IF: | .WORD | FBUF |
| 489 | 147614 | 000400 | | NSPDSP: | .WORD | NSPDIS |
| 490 | 147616 | 000020 | | NY: | .WORD | NYS |
| 491 | 147620 | 000000 | | ITH: | .WORD | 0 |
| 492 | 147622 | 134600 | | IC: | .WORD | ICBUF |
| 493 | 147624 | 136670 | | IS: | .WORD | ISBUF |
| 494 | 147626 | 000000 | | COSORG: | .WORD | 0 |
| 495 | 147630 | 000000 | | SINORG: | .WORD | 0 |
| 496 | 147632 | 000000 | | IGPTR: | .WORD | 0 |
| 497 | 147634 | 000000 | | THEREL: | .WORD | 0 |
| 498 | 147636 | 000000 | | XGPPTR: | .WORD | 0 |
| 499 | 147640 | 000000 | | XCMPTR: | .WORD | 0 |
| 500 | 147642 | 000000 | | IYT: | .WORD | 0 |
| 501 | 147644 | 000000 | | SAVSTK: | .WORD | 0 |
| 502 | 147646 | 000000 | | XYMAX: | .WORD | 0 |
| 503 | 147650 | 000000 | | XYMIN: | .WORD | 0 |
| 504 | 147652 | 000000 | | YTOP: | .WORD | 0 |
| 505 | 147654 | 002000 | | YBOT: | .WORD | 0 |
| 506 | 147656 | 000000 | | ADCTR1: | .WORD | 0 |
| 507 | 147660 | 000000 | | R4MAX: | .WORD | 0 |
| 508 | 147662 | 000000 | | FXYADR: | .WORD | 0 |
| 509 | 147664 | 000020 | | GPBTSR: | .WORD | 2*LGPREC |
| 510 | 147666 | 000000 | | LOPROD: | .WORD | 0 |
| 511 | 147670 | 000000 | | FXYAT2: | .WORD | 0 |
| 512 | 147672 | 000000 | | HIBITS: | .WORD | 0 |
| 513 | 147674 | 000000 | | ISPTR: | .WORD | 0 |
| 514 | 147676 | 000000 | | ADCTRM: | .WORD | 0 |
| 515 | 147700 | 000000 | | XROCTR: | .WORD | 0 |
| 516 | 147702 | 000000 | | TMCNTH: | .WORD | 0 |
| 517 | 147704 | 000000 | | XCOUNT: | .WORD | 0 |
| 518 | 147706 | 000000 | | YCOUNT: | .WORD | 0 |
| 519 | 147710 | 000000 | | YSROAD: | .WORD | 0 |
| 520 | 147712 | 000000 | | YSPTR: | .WORD | 0 |
| 521 | 147714 | 000000 | | THECNT: | .WORD | 0 |
| 522 | 147716 | 000000 | | YSCOLA: | .WORD | 0 |
| 523 | 147720 | 000000 000000 | | SB1: | .WORD | 1,0 |
| 524 | 147724 | 000001 000000 | | SB2: | .WORD | 1,0 |
| 525 | 147730 | 000001 000000 | | SB3: | .WORD | 1,0 |
| 526 | 147734 | 000000 | | YGCNT: | .WORD | 0 |
| 527 | 147736 | 000000 | | GPSEC: | .WORD | 0 |
| 528 | 147740 | 000000 | | GPSRQD: | .WORD | 0 |
| 529 | 147742 | 000000 | | XLVEC: | .WORD | 0 |
| 530 | 147744 | 000000 | | XLPTR: | .WORD | 0 |
| 531 | | | | | | |
| 532 | | 124156' | | | .END | UNDFW |
| 533 | | | | | | |

TABLE V

```
.TITLE UNMFB250
;TASK WHICH MAKES BONE PROJECTIONS FROM EXISTING 258 SECTOR IMAGE.DAT FILE
;
;
;GB ARRAYS ARE 512 WORD SECTOR PAIRS ON DK1:,STARTING AT GBSSEC;
;     ONLY THE 1ST 611 WORDS OF EACH PAIR ARE DATA (NSPSMP=611).
;THE INPUT ARRAY IS READ FROM SY0:(LUN 1) AS FILE IMAGE.DAT, AS
;     256 ROWS OF 256 WORDS EACH, STARTING FROM THE TOP ROW OF
;     THE PICTURE.
;
;     IGP=STARTING ADDRESS OF GB ARRAYS IN CORE
;NOTE: UNMFB IS WRITTEN IN SUCH A WAY THAT OPERAND ADDRESSES
;     MAY BE CALCULATED AS IN MF (USING XLIST,ETC). THEREFORE F IS
;     GIVEN DOUBLE PRECISION SPACE IN FBUF AND GPBUF1 CONTAINS
;     THE LOW 16 BITS OF CALCULATED G-VALUES. THE HIGH 16 BITS ARE
;     STORED IN GPBUF2. WHEN THE G VALUES HAVE BEEN CALCULATED,
;     THEY ARE CONVERTED TO SINGLE PRECISION IN GPBUF1 & WRITTEN TO
;     DK1:.
;     NSPSMP=# OF ELEMENTS (L VALUES) IN A GB(L,THETA)
;     NTHE=# OF THETA VALUES OF GB ARRAYS IN CORE
;     IF=STARTING ADDRESS OF F(X,Y) ROWS IN CORE
;     NSPDSP=# OF ROWS OR COLUMNS IN F(X,Y)
;     NY=# OF Y VALUES OF F(X,Y) IN CORE
;     IC=STARTING ADDRESS OF COS*DCM/ACM TABLE
;     IS=STARTING ADDRESS OF SIN*DCM/ACM TABLE
;     ITH=INITIAL THETA SUBSCRIPT (FOR 1ST THETA IN CORE)
;     IYT=INITIAL (TOP) Y SUBSCRIPT OF F(X,Y) IN CORE
;
;NSPSMP MUST BE ODD; NSPDSP MUST BE EVEN.
;NSPDSP/NY AND NROWS/NTHE MUST BE INTEGERS
;
        .MCALL  FSRSZ$,FDBDF$,FDBDG$,FDOP$A,NMBLK$
        .MCALL  QIOS$,READ$
        .MCALL  FDAT$A,FDBKG$A,OPEN$W
        .MCALL  OPEN$R,CLOSE$,GET$S,OPEN$S
        .MCALL  WTSE$S,WTLOG$,EXIT$S,WAIT$
        .LIST   MEB

R0=%0
        R1=%1
        R2=%2
```

```
51  000003              R3=%3
52  000004              R4=%4
53  000005              R5=%5
54  000006              SP=%6
55  000007              PC=%7
56
57  000001              SY0=1
58  000002              DK1=2
59
60  001000              LGREC=512.
61  000777              NSPNAM=511.
62  000400              NSPDIS=256.
63  000014              NTHETS=12.
64  000020              NYS=16.
65  001034              NPROJS=540.
66  000030              GSSEC=24.
67  002120              GPSSEC=2*NPROJS+GSSEC
68  002210              GRSSEC=2*NPROJS+GPSSEC
69  003300              GWSSEC=2*NPROJS+GRSSEC
70
71
72  000055              NTGRPS=NPROJS/NTHETS
73  000020              NYGRPS=NSPDIG/NYS
74  001000              FBYTSC=2*NSPDIS
75
76
77  004000              FBUFSZ=4*NSPDIS*NYS
78  030000              GPB1SZ=2*LGPREC*NTHETS
79  000000              CPB2SZ=GPB1SZ
80  014000              XCBFSZ=2*NTHETS*NSPDIS
81  000600              YSBFSZ=2*NPROJS*NYS
82  002070              IGBFSZ=2*NPROJS
83  002070              ISBFSZ=2*NPROJS
84  003000              XLSTSZ=2*3*NSPDIS
85
86
87
88
89                     ;USE FBUF AS SCRATCH AREA FOR FCS GETS AT START OF PROGRAM:
90  000000             FBUF:
91  000000 000572       FDBIC:  FSIGZS  1,512.
92  000000 001000              FDBDFC  ,RECBUF,512.
93  000140                     FDBCSA
94  000022                     .WORD   RECBUF
95  000026 000572              .WORD   512.
96  000042 001              FDBP3A  SY0,,ICNAM
97  000046 000140              .BYTE   SY0
98                            .WORD   ICNAM
99  000146            ICNAM:   .RAD50  IC,DAT
    000150 034270
    000154 000000              .WORD   0
```

```
                                    .WORD    0
                                    .RAD50   /DAT/

98
 99  000152 000000
100  000154 014474
     000176          FDDIS:  FDBDF$
     000220 000572'          FDRCSA   ,RECBUF,512.
     000216 010000           .WORD    RECBUF
101  000236 001              .WORD    512.
     000240 000336'          FDOPSA   SY0,,ISNAM
102  000244 001              .BYTE    SY0
     000336                  .WORD    ISNAM
     000344 035470           NMBLK$   IS,DAT
     000346 000000           .RAD50   /IS/
     000350 000000           .WORD    0
     000352 014474           .WORD    0
                             .RAD50   /DAT/
103
104  000374          FDDXL:  FDBDF$
105  000534 000572'          FDRCSA   ,RECBUF,512.
     000416 010000           .WORD    RECBUF
     000414                  .WORD    512.
106  000436 001              FDOPSA   SY0,,XLNAM
     000442 000534'          .BYTE    SY0
                             .WORD    XLNAM
107  000534 113751  074740   NMBLK$   XLIST,DAT
     000542 000000           .RAD50   /XLIST/
     000546 014474           .WORD    0
                             .RAD50   /DAT/
108
109  000572          RECBUF: .BLKB    512.
110
111                          =FRUF+FBUFSZ
112  000572 040000'  CPBUF1: .BLKB    CPB1SZ
113  040000                  GPBUF2: .BLKB    GPB2SZ
114  070000          XCBUF:  .BLKB    XCBFSZ
115  120000          YSBUF:  .BLKB    YSBFSZ
116  134000          ICBUF:  .BLKB    ICBFSZ
117  134600          ISBUF:  .BLKB    ISBFSZ
118  136670          XLBUF:  .BLKB    XLSTSZ
119  140760
120
121                  FDBIMG: FDBDF$
122  143760                  FDATSA   R.FIX,FD.BLK,512.,-256.
123  144120 000C             .BYTE    R.FIX
     143760 000C             .WORD    FD.BLK
     143761 001000           .WORD    512.
     143762 177376           .WORD    -256.
124  144014          FDRCSA           FD.RWM,FRUF,512.
     143776 000C             .BYTE    FD.RWM
     144002 000000           .WORD    FRUF
     144000 010000           .WORD    512.
125  144120          FDRCSA  FRUF,512.,,3,SB3
     144002 000000           .WORD    FRUF
```

```
                                                            .WORD    512.
       144000  001000                                       .BYTE    3
       144010  003                                           .WORD    147722'
       144004  147722'                                      .BYTE    SY0
       144020  001                                   FROPGA  SY0,,IMGNAM,FO.RD
       144022  144120'                                      .BYTE    SY0
       144026  000C                                          .WORD    IMGNAM
126    144023                                                .BYTE    FO.RD
       144120  035111                                IMGNAM: RAD50   IMAGE,DAT,1
       144126  000000                                        .RAD50  /IMAGE/
127    144126  026210                                        .WORD   0
       144132  014474                                        .RAD50  /DAT/
       144134  000001                                        .WORD   1

;MACRO TO LOAD A BUFFER WITH CONSTANTS FROM DISK:
        .MACRO   LOAD$  FDB,BFSIZ,BFSA
        MOV      FDB,R0                     ;FILE DESCRIPTOR BLOCK ADR
        MOV      BFSIZ,R1                   ;SIZE (BYTES) OF DEST BUFFER
        MOV      BFSA,R2                    ;STARTING ADR OF DESTINATION
        JSR      PC,RDNWDS
        .ENDM

;MACRO TO TEST FOR I/O ERRORS
        .MACRO   TSTIO$  SB
        .ENABL   LSB
        CMPB     SB,#IS.SUC                 ;TEST FOR SUCCESSFUL I/O
        BEQ      10
        MOV      SB,R0
        JSR      PC,IOERR                   ;ABORT IF I/O WAS BAD
10:                                         ;CONTINUE
        .DSABL   LSB
        .ENDM

UNMFB:
;READ IC.DAT, IS.DAT, & XLIST.DAT INTO CORE
       144156                                LOAD$  #FDBIC,#ICBFSZ,#ICBUF
       144156  012700  000000                MOV    #FDBIC,R0                ;FILE DESCRIPTOR BLOCK ADR
       144162  012701  002070                MOV    #ICBFSZ,R1               ;SIZE (BYTES) OF DEST BUFFER
       144166  012702  134600                MOV    #ICBUF,R2                ;STARTING ADR OF DESTINATION
       144172  004767  003246                JSR    PC,RDNWDS
154    144176                                LOAD$  #FDBIS,#ISBFSZ,#ISBUF
       144176  012700  000176                MOV    #FDBIS,R0                ;FILE DESCRIPTOR BLOCK ADR
       144202  012701  002070                MOV    #ISBFSZ,R1               ;SIZE (BYTES) OF DEST BUFFER
       144206  012702  136670                MOV    #ISBUF,R2                ;STARTING ADR OF DESTINATION
       144212  004767  003226                JSR    PC,RDNWDS
155    144216                                LOAD$  #FDBXL,#XLSTSZ,#XLBUF
       144216  012700  000374                MOV    #FDBXL,R0                ;FILE DESCRIPTOR BLOCK ADR
       144222  012701  003000                MOV    #XLSTSZ,R1               ;SIZE (BYTES) OF DEST BUFFER
       144226  012702  140760                MOV    #XLBUF,R2                ;STARTING ADR OF DESTINATION
       144232  004767  003206                JSR    PC,RDNWDS
```

```
                                    ;CALCULATE FACTOR FOR PRO-RATING MU VALUES
156   144236   016701   003326              MOV     ALPHSH,R1
157   144242   016703   003320              MOV     THRSH2,R3
158   144246   166763   003312              SUB     THRSH1,R3
159   144252   016704   003304              MOV     THRSH2,R4
160   144256   005005                       CLR     R5
161   144262   054401                       NEG     R1
162   144266   073401                       ASHC    R1,R4                ;(T2/(T2-T1))*2**(-ALPHSH)
163   144264   071403                       DIV     R3,R4
164   144264   910467   003300              MOV     R4,ALPHA
165   144266
166                                 ;SET UP TO DO FULL PROJECTION
167   144272   012767   040000'  003276     MOV     #GPBUF1,IGP
168   144300   012767   000001   003304     MOV     #1,ITH1
169   144306   012767   000055   003260     MOV     #NTGRPS,THGCNT
170   144314   016767   003236   003406     MOV     GOUTSS,GPSEC
171
172                                 ;
173                                 ;PREPARE TO CALCULATE 1 G-GROUP:
174   144322   012700   030000             CALGG:   MOV     #GP1SZ,R0
175   144326   012701   040000'            CLRGLP:  MOV     #GPBUF1,R1
176   144332   005021                               CLR     (R1)+
177   144334   077002                               SOB     R0,CLRGLP
178   144336   012767   000030   003362             MOV     #NYGRPS,YGCNT    ;ERASE G BUFFER PAIR (LO,HI)
179   144344   012767   000030   003262             MOV     #RSPOIS,IYT      ;SET UP FOR 1ST Y-GROUP
180   144352   000000                       OPENGR: MOV     #FDBING,... ,ERR
          143760'  000000G  000000G                 MOV     ND,#FO.RD,       MOVB #FO.RD,F.FACC(R0)
   144352                                   .IIF    ND,#FO.RD,
   144360                                           JSR     PC,.OPEN
   144364   103002                                  BCC     .+6
   144366   004767   003144                         JSR     PC,ERR
   144372                                 ;
181                                 ;
182                                 ;SKIP PAST 1ST 2 RECORDS OF 256 SECTOR FILE
183   144376   012704   000000'             MOV     #FBUF,R4
184   144402   012700   143760'             READ$:  MOV     #FDBING,R4,..,#3,#SB3,,ERR
          000022                                    MOV     NB,R4,       MOV    R4,F.BKDS+2(R0)
   144402   010460                          .IIF    NB,R4,
   144406   112760   000003   147722'       .IIF    NB,#3,       MOVB #3,F.BKEF(R0)
   144414   012760   000000G                .IIF    NB,#SB3,     MOV       #SB3,F.BKST(R0)
   144422   004767   003102                         JSR     PC,.READ
                                                    BCC     .+6
   144430   004767   003144                         JSR     PC,ERR
                                                    JSR     PC,WAIT
185   144434   012700   143760'             MOV     #FDBING,R0
   144440   112760   000003   006050        .IIF    NB,#3,       MOVB #3,F.EFN(R0)
   144446   012760   147722'  000000G       .IIF    NB,#SB3,     MOV       #SB3,F.BKST(R0)
   144456   004767                          JSR     PC,WAIT
                                            TST10$:
186   144464   126727   001404   000000G    CMPB    SB3,#IS.SUC        ;TEST FOR SUCCESSFUL I/O
   144472   001404                          BEQ     10
   144474   016700   003232                 MOV     SB3,R0
   144500   004767   003046                 JSR     PC,IOERR           ;ABORT IF I/O WAS BAD
187   144504   012704   000000'             MOV     #FBUF,R4
```

```
                                        READ3:  MOV     #FDBIMG,R4,,,#3,#SB3,,ERR
188 144510  012700  143760'                     MOV     #FDBIMG,R0
    144514  010460  000022                      .IIF    NB,R4,   MOV    R4,F.DKDS+2(R0)
    144520  112760  000003  000050              .IIF    NB,#3,   MOVB   #3,F.DKEF(R0)
    144526  012760  147722' 000024              .IIF    NB,#SB3,        MOV    #SB3,F.DKST(R0)
    144534  004767  000000C                     JSR     PC,.READ
    144540  103002                              BCC     .+6
    144542  004767  002774                      JSR     PC,ERR
189 144546  012700  143760'                     MOV     #FDBIMG,#3,#SB3
    144552  112760  000003  000050              .IIF    NB,#3,   MOVB   #3,F.EFN(R0)
    144560  012760  147722' 000024              .IIF    NB,#SB3,        MOV    #SB3,F.DKST(R0)
    144566  004767  000000C                     JSR     PC,.WAIT
190 144572                                      TSTIO$  SB3
    144572  126727  001124                      CMPB    SB3,#IS.SUC        ;TEST FOR SUCCESSFUL I/O
    144600  001404                              BEQ     1$
    144602  016700  003114                      MOV     SB3,R0
    144606  004767  002740                      JSR     PC,IOERR            ;ABORT IF I/O WAS BAD

;READ AN F-GROUP (Y-GROUP)
                                        READFG: MOV     #NYS,R5
                                        READLP: MOV     #FBUF,R4
191 144612  012705  000020                      MOV     #FDBIMG,R4,,,#3,#SB3,,ERR
192 144616  012704  000000'                     MOV     #FDBIMG,R0
193                                             .IIF    NB,R4,   MOV    R4,F.DKDS+2(R0)
194 144622                                      .IIF    NB,#3,   MOVB   #3,F.DKEF(R0)
    144622  012700  143760'                     MOV     #SB3,F.DKST(R0)
    144626  010460  000003                      .IIF    NB,#SB3,        MOV    #SB3,F.DKST(R0)
    144632  112760  000003  000060              JSR     PC,.READ
    144640  012760  147722' 000024              BCC     .+6
    144646  004767  000000C                     JSR     PC,ERR
    144652  103002                              
    144654  004767  002662                      
195 144660                                      WAIT$   SB3
    144660  012700  143760'                     MOV     #FDBIMG,#3,#SB3
    144664  000000  000050                      .IIF    NB,#3,   MOVB   #3,F.EFN(R0)
    144672  012760  147722' 000024              .IIF    NB,#SB3,        MOV    #SB3,F.DKST(R0)
    144700  004767  000000C                     JSR     PC,.WAIT
196 144704                                      TSTIO$  SB3
    144704  125727  003012                      CMPB    SB3,#IS.SUC        ;TEST FOR SUCCESSFUL I/O
    144712  001404                              BFQ     1$
    144714  016700  003002                      MOV     SB3,R0
    144720  004767  002626                      JSR     PC,IOERR            ;ABORT IF I/O WAS BAD
    144724  062704  001000                      ADD     #FBYTSC,R4
    144730  077504                              SOB     R5,READLP
    144732  012701  040000                      MOV     #FBUFSZ,R1          ;EXPAND F INTO DBL PREC (LIKE MF)
197 144736  066201                              ASR     R1
198 144740  006201                              ASR     R1
199 144742  012703  040000'                     MOV     #FBUF+F9UFSZ,R3     ;OUTPUT POINTER
200 144746  012702  020000'                     MOV     #FBUFSZ/2+FBUF,R2   ;INPUT POINTER
201 144752  014243                              MOV     -(R2),-(R3)
202 144754  005043                              CLR     -(R3)
203 144756  077103                              SOB     R1,EXPDLP

;PROJECT EACH NU IN THE F GROUP INTO ALL PROJECTIONS:
                                        PROCFG: MOV     #NSPDIS,R1
209 144760  012701  000400                      MOV     #NSPDIS,R1
210 144764  166701  002644                      SUB     IYT,R1
```

```
211  144770  070127  000006              MUL     #6,R1
213  144774  062701  140760'             ADD     #XLBUF,R1           ;POINT TO APPROP PART OF XLIST
214  145000  010167  002730              MOV     R1,XLVEC
215
216  145004  004767  000334              JSR     PC,PROJEC           ;CALL PROJEC(IGP,ITHI,IYT,XLVEC)
217
218  145010  162767  000020  002616      SUB     #NYS,IYT
219  145014  005367  002704              DEC     YGCNT               ;ARE THERE MORE F-GROUPS IN IMAGE?
220  145022  003273                      BGT     READFG              ;BRANCH IF THERE ARE
221
                                         CLOSE$                      ;ELSE CLEANUP & WRITE THE PROJECTIONS
     145024  012700  147760'             MOV     #FDBING,R0
     145030  004767  000000G             JSR     PC,.CLOSE
     145034  103002                      BCC     .+6
     145036  004767  002500              JSR     PC,ERR
222  145042  012703  040000              MOV     #GPBUF1,R3          ;LO 16 BIT POINTER
223  145046  012702  070000'             MOV     #GPBUF2,R2          ;HI 16 BIT POINTER
224  145052  012701  014000              MOV     #GPB1SZ/2,R1
225  145056  012204                      MOV     (R2)+,R4
226  145060  113905                      MOV     (R3),R5
227  145062  073467  002472              ASHC    GSHIFT,R4
228  145066  070467  002470              MUL     GFACT,R4
229  145072  010423                      MOV     R4,(R3)+
230  145074  077110                      SOB     R1,NORMLP           ;SAVE SINGLE PREC NORMALIZED RESULT
231
232                                    ;FILTER OUT THE 256 CYCLE RIPPLE:
233  145076  012705  000014              MOV     #NTHFTS,R5
234  145102  012702  040000'             MOV     #GPBUF1,R2          ;START OF 1ST PROJECTION
235  145106  011200                      PREFLP: MOV     (R2),R0
236  145110  066000                      ADD     R0,R0
237  145112  066200  000000              ADD     2(R2),R0
238  145116  010862                      MOV     R0,GPB1SZ(R2)
239  145122  062702  000002              ADD     #2,R2
240  145126  012701  007776              MOV     #RSPSAN-1,R1
241  145132  166290  177776              SUB     #-2(R2),R0
242  145136  010200                      FILTLP: MOV     (R2),R0
243  145140  066290  000000              ADD     2(R2),R0
244  145142  066200  000002              ADD     2(R2),R0
245  145146  010862  000000              MOV     R0,GPB1SZ(R2)
246  145152  062702  000002              ADD     #2,R2
247  145156  077113                      SOB     R1,FILTLP
248  145160  062702  000002              ADD     #2,R2
249  145164  077530                      SOB     R5,PREFLP
250
251                                    Q10$$:
     145166  005046                      CLR     -(SP)
     145170  016746  002534              MOV     #IO.WLB,#DK1,#1,,<#SD1,,<#GPBUF2,#GPB1SZ,,#0,GPSEC,ERR
     145174  005046                      CLR     GPSEC,-(SP)
     145176  005046                      CLR     -(SP)
     145200  012746  030000              MOV     #GPB1SZ,-(SP)
     145204  012746  070000'             MOV     #GPBUF2,-(SP)
     145210  005046                      CLR     -(SP)
     145212  012746  147712'             MOV     #SD1,-(SP)
```

```
145216  005046                      CLR    -(SP)
145220  112716  000001               MOVB   #1,(SP)
145224  012746  000002               MOV    #BK1,-(SP)
145230  012746  000000C              MOV    #IO.WLD,-(SP)
145234  012746                       MOV    (PC)+,-(SP)
145236  001                          .BYTE  1,12.
145240  014                          ENT    ^O<377>
145242  104377                       BCC    .+6
145244  103002                       JSR    PC,ERR
    252 004767  002272               WTSESS
145250  012746  000001               MOV    #1,-(SP)
145254  012746                       MOV    (PC)+,-(SP)
145256  051                          .BYTE  41.,2
145260  104377                       ENT    ^O<377>
    253                       TSTIOS SB1
145262  126727  002424  000000C     CMPB   SB1,#IS.SUC    ;TEST FOR SUCCESSFUL I/O
145270  001404                       BEQ    13
145272  016700  002414               MOV    SB1,R0
145276  004767  002350               JSR    PC,IOERR       ;ABORT IF I/O WAS BAD 145302  062767  000030  002420      ADD    #2*NTHETS,CPSEG ;SET UP FOR NEXT THETA GROUP
    255
    256 145310  062767  000014  002274  ADD    #NTHETS,ITHI  ;ARE THERE MORE TO CALCULATE?
    257 145316  005367  002352       DEC    THGCNT
    258 145322  003402                BLE    TERM
    259 145324  000167  176772       JMP    CALCG          ;RETURN IF THERE ARE
    260
    261                      ;ALL DONE!
    262                      TERM:  EXIT$S
145330  012746  000001               MOV    (PC)+,-(SP)
145332  063                          .BYTE  51.,1
145334  104377                       ENT    ^O<377>        ;THE END !

263                             EXIT$S
    264 145336  012746  000001       MOV    (PC)+,-(SP)
145342  063                          .BYTE  51.,1
145344  104377                       ENT    ^O<377>

265
    266                      ;PROJECTION SUBROUTINE (USES ICP,ITHI,IYT,XLVEG)
    267 145344  016700  002242      PROJEC: MOV    ITHI,R0
    268 145350  005300                       DEC    R0
    269 145352  006300                       ASL    R0
    270 145354  010001                       MOV    R0,R1
    271 145356  066700  002232      ADD    IC,R0
    272 145362  010367  002224      MOV    R0,COSORG     ;INIT ADR OF COS VALUES TO USE
    273 145366  066701                       ADD    IS,R1
    274 145372  010167  002232      MOV    R1,SINORG     ;INIT ADR OF SIN VALUES TO USE
    275 145376  016767  002332       MOV    XLVEG,XLPTR   ;INIT ADR OF XLIST VALUES TO USE
    276
    277                      ;COMPUTE MATRIX OF X*COS(THETA) VALUES (NTHE X NSPDSP)
    278 145404  016767  002210  002212 MOV  COSORG,ICPTR  ;INITIALIZE IC POINTER FOR ITHI
    279 145412  005067  002210       CLR    THEREL        ;THETA (RELATIVE)
    280 145416  010667  002214       MOV    SP,SAVSTK     ;SAVE STACK POINTER
    281 145422  016705                       MOV    NTHE,SP
```

| | | | | | | |
|---|---|---|---|---|---|---|
| 282 | 145426 | 065306 | | ASL | SP | ;BYTES PER ROW OF XGBUF |
| 283 | 145430 | 010667 | 002240 | MOV | SP,TWONTH | |
| 284 | 145434 | 017700 | 002164 | MOV | @ICPTR,R0 | ;GET 1ST VALUE OF COSINE |
| 285 | | | | ;ROW (OVERALL) LOOP: | | |
| 286 | 145440 | 062767 | 000002 | XCRLP: ADD | #2,ICPTR | ;SET POINTER FOR NEXT THETA |
| 287 | 145444 | 016701 | 002134 | MOV | NSPDSP,R1 | ;SET X COUNTER |
| 288 | 145452 | 006201 | | ASR | R1 | |
| 289 | 145454 | 010303 | | MOV | R0,R3 | |
| 290 | 145460 | 005403 | | NEG | R3 | ;1ST X = -1 + DELTA X, |
| 291 | 145462 | 006702 | | SXT | R2 | |
| 292 | 145464 | 006300 | | ASL | R0 | ;DELTA X = 2 |
| 293 | 145466 | 016704 | 002136 | MOV | THEREL,R4 | ;INITIALIZE UP & DOWN VECTORS: |
| 294 | 145472 | 006304 | | ASL | R4 | |
| 295 | 145474 | 062704 | 120000 | ADD | #XCBUF,R4 | ;POINT TO TOP OF COLUMN |
| 296 | 145500 | 016705 | 002104 | MOV | NSPDSP,R5 | |
| 297 | 145504 | 070567 | 002074 | MUL | NTHE,R5 | |
| 298 | 145506 | 060405 | | ADD | R4,R5 | |
| 299 | 145510 | 010567 | 002114 | MOV | R5,XCPPTR | ;POINTER FOR POSITIVE X VALUES |
| 300 | 145514 | 160605 | | SUB | SP,R5 | |
| 301 | 145516 | 010567 | 002110 | MOV | R5,XCMPTR | ;POINTER FOR NEGATIVE X VALUES |
| 302 | | | | ;COLUMN LOOP: | | |
| 303 | 145522 | 005700 | | XCLLP: TST | R0 | |
| 304 | 145524 | 006705 | | SXT | R5 | |
| 305 | 145526 | 060303 | | ADD | R3,R3 | |
| 306 | 145530 | 060505 | | ADD | R5,R5 | |
| 307 | 145532 | 060502 | | ADD | R5,R2 | |
| 308 | 145534 | 010204 | | MOV | R2,R4 | |
| 309 | 145536 | 010305 | | MOV | R3,R5 | |
| 310 | 145540 | 073427 | 000005 | ASHC | #5,R4 | |
| 311 | 145542 | 006305 | | ASL | R5 | |
| 312 | 145544 | 005504 | | ADC | R4 | |
| 313 | 145546 | 010477 | 002054 | MOV | R4,@XCPPTR | |
| 314 | 145552 | 005404 | | NEG | R4 | |
| 315 | 145554 | 010477 | 002050 | MOV | R4,@XCMPTR | |
| 316 | 145560 | 160667 | 002044 | SUB | SP,XCMPTR | |
| 317 | 145564 | 060667 | 002036 | ADD | SP,XCPPTR | |
| 318 | 145570 | 077125 | | SOB | R1,XCLLP | |
| 319 | | | | | | |
| 320 | 145574 | 017700 | 002034 | MOV | @ICPTR,R0 | ;GET NEXT COS |
| 321 | 145600 | 005267 | 002032 | INC | THEREL | |
| 322 | 145604 | 026767 | 002016 | CMP | THEREL,NTHE | |
| 323 | 145612 | 002712 | | BLT | XCRLP | |
| 324 | | | | | | |
| 325 | 145614 | 016700 | 002014 | MOV | IYT,R0 | |
| 326 | 145620 | 006300 | | ASL | R0 | |
| 327 | 145622 | 166700 | 001760 | SUB | NSPDSP,R0 | |
| 328 | 145626 | 005300 | | DEC | R0 | |
| 329 | 145630 | 010067 | 002010 | MOV | R0,YTOP | ;YTOP=-NSPDSP-1+2*IYT |
| 330 | | | | | | |
| 331 | | | | | | |
| 332 | 145634 | 016760 | 001740 | MOV | NSPSMP,R0 | |
| 333 | 145640 | 005300 | | DEC | R0 | |
| 334 | 145642 | 066700 | 001730 | ADD | R0,IGF | ;IGF+2(NSPSMP-1)/2 |

```
                                        ;ADR OF CENTER OF 1ST C' IN CORE
335  145646  010067          NOV    R0,ADCTRI
336
337                          ;COMPUTE MATRIX OF Y*SIN(THETA)+CENTER ADDRESS CONSTANTS (YSBUF)
338  145652  016767  002006  NOV    SINORG,ISPTR
339  145660  016767  002020  NOV    NTHE,THECNT
340  145666  016706  002002  NOV    TWONTH,SP
341  145672  012767  134000  NOV    #YSBUF,YSCOLA
342  145700  016767  001762  NOV    ADCTRI,ADCTRN
343  145706  017701          NOV    @ISPTR,R1           ;GET SINE
344  145712  006700          SXT    R0                  ;MAKE IT DBL PREC
345  145714  062767  000002  YSRLP: ADD   #2,ISPTR
346  145722  010102          NOV    R1,R2
347  145724  006301          ASL   R1                   ;R0,R1 = DBL PREC INCREMENT IN PRODUCT
348  145726  070267  001712  NUL   YTOP,R2              ;R2,R3 = CURRENT (1ST) PRODUCT
349  145732  016767  001652  NOV   NY,YCOUNT
350  145740  016767  001744  NOV   YSCOLA,YSPTR         ;POINT TO TOP OF A YSBUF COLUMN
351  145746  010204          NOV   R2,R4                ;COPY CURRENT PRODUCT
352  145750  016305          NOV   R3,R5
353  145752  073427  000005  YSCLP: ASHC  #5,R4         ;NORMALIZE & ROUND
354  145756  063305          ASL   R5
355  145760  055504          ADC   R4
356  145762  064704  001702  ADD   ADCTRN,R4           ;ADD CENTER ADR OF C'(THETA)
357  145766  010477  001712  NOV   R4,@YSPTR           ;STORE Y*SIN+CTRADR IN YSBUF
358  145772  060667  001706  ADD   SP,YSPTR            ;ADVANCE TO NEXT (LOWER) Y
359  145776  060103          ADD   R1,R3               ;COMPUTE NEXT PRODUCT
360  146000  005602          SBC   R2
361  146002  160002          SUB   R0,R2
362  146004  005367          DEC   YCOUNT
363  146010  003356  001670  BGT   YSCLP               ;CONTINUE TIL HAVE DONE NY Y'S
364                          ;GET READY FOR NEXT COLUMN (THETA) OF YSBUF:
365  146012  064767  001640  ADD   G2BTSR,ADCTRN
366  146020  062767  000002  001662  ADD   #2,YSCOLA
367  146026  005367  001654  DEC   THECNT
368  146032  003325          BGT   YSRLP
369
370
371                          ;PROJECTION LOOP
372  146034  016767  001636  NOV   NY,YCOUNT
373  146042  012767  134000  001632  NOV   #YSBUF,YSROAD
374
375                          YLP:
376  146050  017767  001576  NOV   @XLPTR,FXYADR       ;ADR OF INITIAL F TO CONTRIB TO
377  146056  016700          NOV   FXYADR,R0
378  146062  063700          ADD   #2,R0
379  146066  010067          NOV   R0,FXYAP2           ;ADR OF LOW ORDER BITS OF F(X,Y)
380  146072  062767  000002  001636  ADD   #2,XLPTR
381  146100  017767  001570  NOV   @XLPTR,XCOUNT       ;# OF X'S TO COMPUTE THIS ROW
382  146106  062767  000002  001622  ADD   #2,XLPTR
383  146114  017700          NOV   @XLPTR,R0
384  146120  062767  000002  001610  ADD   #2,XLPTR
385  146126  016701          NOV   YSROAD,R1
386  146132  017705          NOV   @FXYAP2,R5          ;GET MU VALUE
387  146136  020567          CMP   R5,THRSH1           ;MU > THRSH1?
```

```
388  146142  003003                    BGT    TRYT2                  ;YES
389  146144  005005                    CLR    R5                     ;NO. DON'T CONTRIBUTE TO BONE PROJS
390  146146  000167                    JMP    USER5                  ;GO THROUGH THE MOTIONS FOR POINTERS
391  146152  000567  000032            CMP    R5,THRSH2              ;MU > THRSH2?
392  146156  002402                    BLT    ADJNU                  ;NO. DISTRIBUTE BETWEEN BONE AND S.T.
393  146160  000167  000020            JMP    USER5                  ;YES. USE R5 AS IS
394  146164  166705  000020    ADJNU:  SUB    THRSH1,R5              ;MU-THRSH1
395  146170  070504            TRYT2:  MUL    R5,R4
396  146172  070467  001374            ASHC   ALPHA,R4
397  146174  073467  001374            ASHC   ALPHSH,R4              ;*ALPHA
398  146200  010405                    MOV    R4,R5
399  146202  010405            USER5:  MOV    R5,R5
400  146204  010505                    MOV    R5,R5
401  146206  006704                    SXT    R4
402           ;INNER "LOOP" OVER THETA:
403           ;DOTHIS:   .NEPT NTHETS
404  146210  000014            .ENABL  LSB
405                                    MOV    (R0)+,R2               ;GET X*COS
406                                    ADD    (R1)+,R2               ;ADD Y*SIN + CENTER ADDRESS
407                                    ROR    R2
408                                    BCS    1$                     ;BRANCH IF ADDRESS IS BORDERLINE
409                                    ASL    R2                     ;POINT TO LEAST SIG 16 BITS OF G
410                                    ADD    R2                     ;DO DBL PREC ADD TO 1 POINT
411                                    ADC    R5,(R2)
412                                    ADD    R4,GPB1SZ(R2)
413                                    BR     2$                     ;REJOIN MAINSTREAM
414  1$:                                ASR    R5                    ;TEMPORARILY SCALE NU TO NU/2
415                                    ASL    R2
416                                    ADD    R5,(R2)
417                                    ADC    CPB1SZ(R2)
418                                    ADD    R4,CPB1SZ(R2)
419                                    ADD    #2,R2
420                                    ADD    R5,(R2)                ;CONTRIBUTE NU/2 TO 2 POINTS
421                                    ADC    CPB1SZ(R2)
422                                    ADD    R4,GPB1SZ(R2)
423                                    ASL    R5                     ;RESTORE NU TO ORIG SCALING
424  2$:      .DSABL LSB
425           .ENDM
146210  122002                   MOV    (R0)+,R2                     ;GET X*COS
146212  062102                   ADD    (R1)+,R2                     ;ADD Y*SIN + CENTER ADDRESS
146214  006002                   ROR    R2
146216  103407                   BCS    1$                           ;BRANCH IF ADDRESS IS BORDERLINE
146220  006302                   ASL    R2                           ;POINT TO LEAST SIG 16 BITS OF G
146222  066512                   ADD    R5,(R2)                      ;DO DBL PREC ADD TO 1 POINT
146224  005562  030000           ADC    GPB1SZ(R2)
146230  060462  030000           ADD    R4,CPB1SZ(R2)
146234  000417                   BR     2$                           ;REJOIN MAINSTREAM
146236  072005            1$:    ASR    R5                           ;TEMPORARILY SCALE NU TO NU/2
146240  006302                   ASL    R2
146242  066512                   ADD    R5,(R2)
146244  005562  030000           ADC    CPB1SZ(R2)
146250  060462  030000           ADD    R4,GPB1SZ(R2)
146254  062702  000002           ADD    #2,R2                        ;CONTRIBUTE NU/2 TO 2 POINTS
```

```
146260  0605512  030000           ADD   R5,(R2)           ;RESTORE NU TO ORIG SCALING
146262  0055562  030000           ADC   GPDISZ(R2)
146266  0604462                   ADD   R4,GPDISZ(R2)     ;GET X*COS
146272  0063305                   ASL   R5                ;ADD Y*SIN + CENTER ADDRESS
146274  0120002                   MOV   (R0)+,R2
146276  0622102                   ADD   (R1)+,R2
146300  0060002                   ROR   R2
146302  103407                    BCS   10                ;BRANCH IF ADDRESS IS BORDERLINE
146304  0063302                   ASL   R2                ;POINT TO LEAST SIG 16 BITS OF G
146306  0605512                   ADD   R5,(R2)           ;DO DBL PREC ADD TO 1 POINT
146310  0055562  030000           ADC   GPDISZ(R2)
146314  0604462  030000           ADD   R4,GPDISZ(R2)
146320  000417                    BR    20                ;REJOIN MAINSTREAM
146322  0063305              10:  ASL   R5                ;TEMPORARILY SCALE NU TO NU/2
146324  0063302                   ASL   R2
146326  0605512                   ADD   R5,(R2)           ;CONTRIBUTE NU/2 TO 2 POINTS
146330  0055562  030000           ADC   GPDISZ(R2)
146334  0604462  030000           ADD   R4,GPDISZ(R2)
146340  0627022                   ADD   #2,R2
146344  0605512                   ADD   R5,(R2)
146346  0055562  030000           ADC   GPDISZ(R2)
146352  0604462  030000           ADD   R4,GPDISZ(R2)
146356  0063305                   ASR   R5                ;RESTORE NU TO ORIG SCALING
146360  0120002                   MOV   (R0)+,R2          ;GET X*COS
146362  0622102                   ADD   (R1)+,R2          ;ADD Y*SIN + CENTER ADDRESS
146364  0060002                   ROR   R2
146366  103407                    BCS   10                ;BRANCH IF ADDRESS IS BORDERLINE
146370  0063302                   ASL   R2                ;POINT TO LEAST SIG 16 BITS OF G
146372  0605512                   ADD   R5,(R2)           ;DO DBL PREC ADD TO 1 POINT
146374  0055562  030000           ADC   GPDISZ(R2)
146400  0604462  030000           ADD   R4,GPDISZ(R2)
146404  000417                    BR    20                ;REJOIN MAINSTREAM
146406  0063305              19:  ASL   R5                ;TEMPORARILY SCALE NU TO NU/2
146410  0063302                   ASL   R2
146412  0605512                   ADD   R5,(R2)           ;CONTRIBUTE NU/2 TO 2 POINTS
146414  0055562  030000           ADC   GPDISZ(R2)
146420  0604462  030000           ADD   R4,GPDISZ(R2)
146424  0627022  000002           ADD   #2,R2
146430  0605512                   ADD   R5,(R2)
146432  0055562  030000           ADC   GPDISZ(R2)
146436  0604462  030000           ADD   R4,GPDISZ(R2)
146442  0063305                   ASR   R5                ;RESTORE NU TO ORIG SCALING
146444  0120002                   MOV   (R0)+,R2          ;GET X*COS
146446  0622102                   ADD   (R1)+,R2          ;ADD Y*SIN + CENTER ADDRESS
146450  0060002                   ROR   R2
146452  103407                    BCS   10                ;BRANCH IF ADDRESS IS BORDERLINE
146454  0063302                   ASL   R2                ;POINT TO LEAST SIG 16 BITS OF G
146456  0605512                   ADD   R5,(R2)           ;DO DBL PREC ADD TO 1 POINT
146460  0055562  030000           ADC   GPDISZ(R2)
146464  0604462  030000           ADD   R4,GPDISZ(R2)
146470  000417                    BR    20                ;REJOIN MAINSTREAM
146472  0063305              10:  ASR   R5                ;TEMPORARILY SCALE NU TO NU/2
146474  0063302                   ASL   R2
146476  0605512                   ADD   R5,(R2)           ;CONTRIBUTE NU/2 TO 2 POINTS
```

```
146500  055562  030000           ADC  GPB1SZ(R2)
146504  060462  030000           ADD  R4,GPB1SZ(R2)
146510  062702  000002           ADD  #2,R2
146514  060512                   ADD  R5,(R2)
146516  055562  030000           ADC  GPB1SZ(R2)
146522  060462  030000           ADD  R4,GPB1SZ(R2)
146526  006305                   ASL  R5
146530  012002                   MOV  (R0)+,R2
146532  062102                   ADD  (R1)+,R2
146534  066002                   ROR  R2
146536  103407                   BCS  1$
146540  006302                   ASL  R2
146542  060512                   ADD  R5,(R2)       ;RESTORE MU TO ORIG SCALING
146544  055562  030000           ADC  GPB1SZ(R2)    ;GET X*COS
146550  060462  030000           ADD  R4,GPB1SZ(R2) ;ADD Y*SIN + CENTER ADDRESS
146554  062702  000002           ADD  #2,R2
146560  060512                   ADD  R5,(R2)
146562  055562  030000           ADC  GPB1SZ(R2)
146564  060462  030000           ADD  R4,GPB1SZ(R2)
146570  000417                   BR   2$            ;BRANCH IF ADDRESS IS BORDERLINE
146574  006205                   ASR  R5            ;POINT TO LEAST SIG 16 BITS OF C
146600  006302                  1$: ASL  R2           ;DO DBL PREC ADD TO 1 POINT
146602  060512                   ADD  R5,(R2)
146604  055562  030000           ADC  GPB1SZ(R2)
146606  060462  030000           ADD  R4,GPB1SZ(R2)
146612  006305                   ASL  R5            ;REJOIN MAINSTREAM
146614  012002                   MOV  (R0)+,R2      ;TEMPORARILY SCALE MU TO MU/2
146616  062102                   ADD  (R1)+,R2
146620  066002                   ROR  R2
146622  103407                   BCS  1$
146624  006302                   ASL  R2
146626  060512                   ADD  R5,(R2)       ;CONTRIBUTE MU/2 TO 2 POINTS
146630  055562  030000           ADC  GPB1SZ(R2)
146634  060462  030000           ADD  R4,GPB1SZ(R2)
146640  062702  000002           ADD  #2,R2
146644  060512                   ADD  R5,(R2)
146646  055562  030000           ADC  GPB1SZ(R2)
146652  060462  030000           ADD  R4,GPB1SZ(R2)
146656  000417                   BR   2$
146662  006205                   ASR  R5            ;RESTORE MU TO ORIG SCALING
146664  006302                  1$: ASL  R2           ;GET X*COS
146666  060512                   ADD  R5,(R2)       ;ADD Y*SIN + CENTER ADDRESS
146670  055562  030000           ADC  GPB1SZ(R2)
146674  060462  030000           ADD  R4,GPB1SZ(R2)
146700  012002                   MOV  (R0)+,R2
146702  062102                   ADD  (R1)+,R2
146704  066002                   ROR  R2
146706  103407                   BCS  1$            ;BRANCH IF ADDRESS IS BORDERLINE
146710  006302                   ASL  R2            ;POINT TO LEAST SIG 16 BITS OF C
146712  060512                   ADD  R5,(R2)       ;DO DBL PREC ADD TO 1 POINT
146714  055562  030000           ADC  GPB1SZ(R2)
146720  060462  030000           ADD  R4,GPB1SZ(R2)
146724  000417                   BR   2$            ;REJOIN MAINSTREAM
146726  006205                  1$: ASR  R5            ;TEMPORARILY SCALE MU TO MU/2
```

```
146730  006302                ASL   R2                          ;CONTRIBUTE NU/2 TO 2 POINTS
146732  065512                ADD   R5,(R2)
146734  065562                ADD   GPB1SZ(R2)
146740  060462                ADD   R4,GPB1SZ(R2)
146744  062702  000002        ADD   #2,R2
146750  060512                ADD   R5,(R2)
146752  065562                ADC   GPB1SZ(R2)
146756  060462                ADD   R4,GPB1SZ(R2)
146762  006305                ASL   R5                          ;RESTORE NU TO ORIG SCALING
146764  012902                MOV   (R0)+,R2                    ;GET X*COS
146766  062102                ADD   (R1)+,R2                    ;ADD Y*SIN + CENTER ADDRESS
146770  006002                ROR   R2
146772  103407                BCS   19                          ;BRANCH IF ADDRESS IS BORDERLINE
146774  006302                ASL   R2                          ;POINT TO LEAST SIG 16 BITS OF C
146776  060512                ADD   R5,(R2)                     ;DO DBL PREC ADD TO 1 POINT
147000  065562                ADD   GPB1SZ(R2)
147004  060462                ADC   R4,GPB1SZ(R2)
147010  000417                BR    20                          ;REJOIN MAINSTREAM
147012  006205        18:     ASR   R5                          ;TEMPORARILY SCALE NU TO NU/2
147014  006302                ASL   R2                          ;CONTRIBUTE NU/2 TO 2 POINTS
147016  060512                ADD   R5,(R2)
147020  065562                ADD   GPB1SZ(R2)
147024  060462                ADD   R4,GPB1SZ(R2)
147030  062702  000002        ADD   #2,R2
147034  060512                ADD   R5,(R2)
147036  065562                ADC   GPB1SZ(R2)
147042  060462                ADD   R4,GPB1SZ(R2)
147046  006305                ASL   R5                          ;RESTORE NU TO ORIG SCALING
147050  012902                MOV   (R0)+,R2                    ;GET X*COS
147052  062102                ADD   (R1)+,R2                    ;ADD Y*SIN + CENTER ADDRESS
147054  006002                ROR   R2
147056  103407                BCS   19                          ;BRANCH IF ADDRESS IS BORDERLINE
147060  006302                ASL   R2                          ;POINT TO LEAST SIG 16 BITS OF C
147062  060512                ADD   R5,(R2)                     ;DO DBL PREC ADD TO 1 POINT
147064  065562                ADD   GPB1SZ(R2)
147070  060462                ADC   R4,GPB1SZ(R2)
147074  000417                BR    20                          ;REJOIN MAINSTREAM
147076  006205        19:     ASR   R5                          ;TEMPORARILY SCALE NU TO NU/2
147100  006302                ASL   R2                          ;CONTRIBUTE NU/2 TO 2 POINTS
147102  060512                ADD   R5,(R2)
147104  065562                ADC   GPB1SZ(R2)
147110  060462                ADD   R4,GPB1SZ(R2)
147114  062702  000002        ADD   #2,R2
147120  060512                ADD   R5,(R2)
147122  065562                ADD   GPB1SZ(R2)
147126  060462                ADC   R4,GPB1SZ(R2)
147132  006305                ASL   R5                          ;RESTORE NU TO ORIG SCALING
147134  012902                MOV   (R0)+,R2                    ;GET X*COS
147136  062102                ADD   (R1)+,R2                    ;ADD Y*SIN + CENTER ADDRESS
147140  006002                ROR   R2
147142  103407                BCS   19                          ;BRANCH IF ADDRESS IS BORDERLINE
147144  006302                ASL   R2                          ;POINT TO LEAST SIG 16 BITS OF G
147146  060512                ADD   R5,(R2)                     ;DO DBL PREC ADD TO 1 POINT
147150  065562  030000        ADC   GPB1SZ(R2)
```

| | | | | | |
|---|---|---|---|---|---|
| 147154 | 060462 | 030000 | | ADD | R4,GPDISZ(R2) ;REJOIN MAINSTREAM |
| 147160 | 060417 | | | BR | 2$ |
| 147162 | 006205 | | | ASR | R5 ;TEMPORARILY SCALE NU TO NU/2 |
| 147164 | 006302 | | | ASL | R2 |
| 147166 | 060512 | | | ADD | R5,(R2) |
| 147170 | 060562 | 030000 | | ADD | R5,GPDISZ(R2) ;CONTRIBUTE NU/2 TO 2 POINTS |
| 147174 | 060462 | 030000 | | ADD | R4,GPDISZ(R2) |
| 147200 | 062702 | 000002 | | ADD | #2,R2 |
| 147204 | 060512 | | | ADD | R5,(R2) |
| 147206 | 060562 | 030000 | | ADD | R5,GPDISZ(R2) |
| 147212 | 060462 | 030000 | | ADD | R4,GPDISZ(R2) |
| 147216 | 006205 | | | ASL | R5 ;RESTORE NU TO ORIG SCALING |
| 147220 | 012902 | | | MOV | (R0)+,R2 ;GET X*COS |
| 147222 | 062102 | | | ADD | (R1)+,R2 ;ADD Y*SIN + CENTER ADDRESS |
| 147224 | 006002 | | | ROR | R2 |
| 147226 | 103407 | | | BCS | 1$ ;BRANCH IF ADDRESS IS BORDERLINE |
| 147230 | 006302 | | | ASL | R2 ;POINT TO LEAST SIG 16 BITS OF G |
| 147232 | 060512 | | | ADD | R5,(R2) ;DO DBL PREC ADD TO 1 POINT |
| 147234 | 005562 | 030000 | | ADC | GPDISZ(R2) |
| 147240 | 060462 | 030000 | | ADD | R4,GPDISZ(R2) |
| 147244 | 000417 | | | BR | 2$ ;REJOIN MAINSTREAM |
| 147246 | 006205 | | 1$: | ASR | R5 ;TEMPORARILY SCALE NU TO NU/2 |
| 147250 | 006302 | | | ASL | R2 |
| 147252 | 060512 | | | ADD | R5,(R2) |
| 147254 | 060562 | 030000 | | ADD | R5,GPDISZ(R2) ;CONTRIBUTE NU/2 TO 2 POINTS |
| 147260 | 060462 | 030000 | | ADD | R4,GPDISZ(R2) |
| 147264 | 062702 | 000002 | | ADD | #2,R2 |
| 147270 | 060512 | | | ADD | R5,(R2) |
| 147272 | 005562 | 030000 | | ADC | GPDISZ(R2) |
| 147276 | 060462 | 030000 | | ADD | R4,GPDISZ(R2) |
| 147302 | 006305 | | | ASL | R5 ;RESTORE NU TO ORIG SCALING |
| 147304 | 005402 | | 2$: | NEG | R2 |
| 147306 | 012902 | | | MOV | (R0)+,R2 ;GET X*COS |
| 147310 | 062102 | | | ADD | (R1)+,R2 ;ADD Y*SIN + CENTER ADDRESS |
| 147312 | 006002 | | | ROR | R2 |
| 147314 | 103407 | | | BCS | 1$ ;BRANCH IF ADDRESS IS BORDERLINE |
| 147316 | 006302 | | | ASL | R2 ;POINT TO LEAST SIG 16 BITS OF G |
| 147320 | 060512 | | | ADD | R5,(R2) ;DO DBL PREC ADD TO 1 POINT |
| 147322 | 005562 | 030000 | | ADC | GPDISZ(R2) |
| 147326 | 060462 | 030000 | | ADD | R4,GPDISZ(R2) |
| 147332 | 000417 | | | BR | 2$ ;REJOIN MAINSTREAM |
| 147334 | 006205 | | 1$: | ASR | R5 ;TEMPORARILY SCALE NU TO 2 POINTS |
| 147336 | 006302 | | | ASL | R2 |
| 147340 | 060512 | | | ADD | R5,(R2) |
| 147342 | 060562 | 030000 | | ADD | R5,GPDISZ(R2) ;CONTRIBUTE NU/2 TO 2 POINTS |
| 147346 | 060462 | 030000 | | ADD | R4,GPDISZ(R2) |
| 147352 | 062702 | 000002 | | ADD | #2,R2 |
| 147356 | 060512 | | | ADD | R5,(R2) |
| 147360 | 005562 | 030000 | | ADC | GPDISZ(R2) |
| 147362 | 060462 | 030000 | | ADD | R4,GPDISZ(R2) |
| 147366 | 006305 | | | ASL | R5 ;RESTORE NU TO ORIG SCALING |
| 147370 | 062767 | 000004 | 000256 | ADD | #4,FXYADR |
| 147376 | 062767 | 000004 | 000256 | ADD | #4,FXYAP2 ;GET SET FOR NEXT IN-CORE F(X,Y) |

```
431  147404  095367  000266           DEC   XCOUNT
432  147410  033402                   BLE   BUMPY
433  147412  000167                   JMP   XLP
434  147416  066767  176510           ADD   TWOINTII,YSROAD     ;RELOOP FOR NEXT X,SAME Y
             000252  000250                                     ;ADVANCE Y ROW STARTING ADDRESS
435  147424  005367  176412           DEC   YCOUNT
436  147430  003402                                BLE   FULKDN
437  147432  000167                                JMP   YLP    ;START NEXT (LOWER) Y ROW
438
439
440  147436  016706  000174   FBLKDN: MOV   SAVSTK,SP          ;RESTORE STACK POINTER
441  147442  000207                   RTS   PC                 ;RETURN TO CALLER
442  ;
443  ;
444  ;
445  ;
446  ;SUBROUTINE TO LOAD A BUFFER WITH CONSTANTS FROM DISK
447  147444  112760           RDNWDS: OPEN@R R0,,,,ERR    MOVB #FO.RD,F.FACC(R0)
     147444  000000  000043           .IIF  NB, ,, , MOVB #FO.RD,
     147452  004767                   JSR   PC,.OPEN
     147456  103602                   BCC   .+6
     147460  004767                   JSR   PC,ERR
448  147464  004767  000056           JSR   R0,.GETS
             004767  000000   GETLP:  GETS$ R0,,GETSQ
     147470  103002                   BCC   .+6
     147472  004767  000044           JSR   PC,ERR
449  ;COPY DATA WORDS READ INTO TARGET BUFFER
450  147476  012704  000574'          MOV   #RECBUF+2,R4      ;WHERE THE DATA STARTS
451  147502  016003  000024           MOV   F.NRBD(R0),R3     ;# OF BYTES JUST READ
452  147506  005303                   DEC   R3
453  147510  095303                   DEC   R3                ;IGNORE 1ST WORD (FCS'S)
454  147512  160301                   SUB   R3,R1             ;# OF DATA BYTES YET TO READ
455  147514  005203                   ASR   R3                ;# OF WORDS TO COPY TO DEST BUFF
456  147516  012422                   MOV   (R4)+,(R2)+       ;COPY FROM RECBUF TO DEST BUFFER
457  147520  077302                   SOB   R3,CTCPLP
458  147522  005701                   TST   R1
459  147524  003357                   BGT   GETLP             ;IS THERE MORE TO READ FROM DISK?
460                                   CLOSE$                  ;YES
     147526  004767  000000           JSR   PC,.CLOSE
461  147532  103002                   BCC   .+6
462  147534  004767  000002           JSR   PC,ERR
463  147540  000207                   RTS   PC
464
465  147542  016700           ERR:    MOV   $DSW,R0
     147546  012401                   MOV   (SP)+,R1
     147550  000000                   HALT
466
467  147552  012601           ICERR:  MOV   (SP)+,R1
468  147554  000000                   HALT
469  ;
470  ;
471  147556  004210           COUTSS:  .WORD  CRSSEC
472  147560  000015           GSHIFT:  .WORD  15
473  147562  060000           GFACT:   .WORD  60000
474  147564  002300           THRSH1:  .WORD  1216.    ;1ST THRESHOLD (ABSOLUTE ROUNDSFIELDS)
```

| Line | Addr | Value | Label | Op | Operand | Comment |
|---|---|---|---|---|---|---|
| 475 | 147566 | 003000 | THRSH2: | .WORD | 1536. | ;2ND THRESHOLD |
| 476 | 147570 | 000004 | ALPHSH: | .WORD | 4 | ;SHIFT COUNT FOR SCALED NU CONTRIBUTIONS |
| 477 | 147572 | 000000 | ALPHA: | .WORD | 0 | ;COMPUTED BY PROGRAM. T2/(T2-T1) *2**16-ALPHSH |
| 478 | | | ; | | | |
| 479 | 147574 | 000000 | THCCNT: | .WORD | 0 | |
| 480 | 147576 | 000000 | ICP: | .WORD | 0 | |
| 481 | 147600 | 000777 | NSPSMP: | .WORD | NSPSAM | |
| 482 | 147602 | 000014 | NTHE: | .WORD | NTHETS | |
| 483 | 147604 | 000000 | IF: | .WORD | FOUF | |
| 484 | 147606 | 000400 | RSPDSP: | .WORD | RSPDIS | |
| 485 | 147610 | 000020 | RY: | .WORD | NYS | |
| 486 | 147612 | 000000 | ITH: | .WORD | 0 | |
| 487 | 147614 | 134600 | IC: | .WORD | IGBUF | |
| 488 | 147616 | 135670 | IS: | .WORD | ISBUF | |
| 489 | 147620 | 000000 | COSORG: | .WORD | 0 | |
| 490 | 147622 | 000000 | SINORG: | .WORD | 0 | |
| 491 | 147624 | 000000 | ICPTR: | .WORD | 0 | |
| 492 | 147626 | 000000 | THEREL: | .WORD | 0 | |
| 493 | 147630 | 000000 | XCPPTR: | .WORD | 0 | |
| 494 | 147632 | 000000 | XCMPTR: | .WORD | 0 | |
| 495 | 147634 | 000000 | IYT: | .WORD | 0 | |
| 496 | 147636 | 000000 | SAVSTK: | .WORD | 0 | |
| 497 | 147640 | 000000 | XTMAX: | .WORD | 0 | |
| 498 | 147642 | 000000 | XYMIN: | .WORD | 0 | |
| 499 | 147644 | 000000 | YTOP: | .WORD | 0 | |
| 500 | 147646 | 000000 | YBOT: | .WORD | 0 | |
| 501 | 147650 | 000000 | ADCTHI: | .WORD | 0 | |
| 502 | 147652 | 000000 | RIMAX: | .WORD | 0 | |
| 503 | 147654 | 000000 | FXYADR: | .WORD | 0 | |
| 504 | 147656 | 020000 | GPBTSR: | .WORD | 2*LGPREC | |
| 505 | 147660 | 000000 | LOPMOD: | .WORD | 0 | |
| 506 | 147662 | 000000 | FXYAP2: | .WORD | 0 | |
| 507 | 147664 | 000000 | HIBYTS: | .WORD | 0 | |
| 508 | 147666 | 000000 | ISPTR: | .WORD | 0 | |
| 509 | 147670 | 000000 | ADCTTR: | .WORD | 0 | |
| 510 | 147672 | 000000 | XROCTR: | .WORD | 0 | |
| 511 | 147674 | 000000 | TWONTH: | .WORD | 0 | |
| 512 | 147676 | 000000 | XCOUNT: | .WORD | 0 | |
| 513 | 147700 | 000000 | YCOUNT: | .WORD | 0 | |
| 514 | 147702 | 000000 | YSROAD: | .WORD | 0 | |
| 515 | 147704 | 000000 | YSPTR: | .WORD | 0 | |
| 516 | 147706 | 000000 | THRCFT: | .WORD | 0 | |
| 517 | 147710 | 000000 | YSCOLA: | .WORD | 0 | |
| 518 | 147712 | 000001 000000 | SB1: | .WORD | 1.0 | |
| 519 | 147716 | 000001 000000 | SB2: | .WORD | 1.0 | |
| 520 | 147722 | 000001 000000 | SB3: | .WORD | 1.0 | |
| 521 | 147726 | 000000 | YCCNT: | .WORD | 0 | |
| 522 | 147730 | 000000 | GPSEG: | .WORD | 0 | |
| 523 | 147732 | 000000 | GPSRQD: | .WORD | 0 | |
| 524 | 147734 | 000000 | XLVEG: | .WORD | 0 | |
| 525 | 147736 | 000000 | XLPTR: | .WORD | 0 | |
| 526 | | | ; | | | |
| 527 | | | | .END | UNMFB | |
| 528 | 144156 | | | | | |

TABLE VI

```
C COMBPR
C
C
C PROGRAM TO COMBINE BONE
C AND SOFT TISSUE PROJECTIONS
C INTO ERROR PROJECTIONS
C
C
C
C
C
C
C
C
C
C FOR COMBPR,LP/SP=COMBPR
C TKB COMBPR=COMBPR
C      MAXBUF=1024
C      UIC=[100,100]
C
C
C
0001       DIMENSION   PRJCB(512),PRJH2O(512),ERRORF(512),
          *            IOSB(2),IPARAM(6),IDSW(1),JPARAM(6),KPARAM(6)
0002       INTEGER     PRJCB,PRJH2O,ERRORF,PRLOOP,CBSSEC,H2SSEC,
          *            EFSSEC,CCOEF,CSYS
0003       IORLB=256*2
0004       IOWLB=256*1
0005       IEFN=1
0006       IDISK=4
0007       ISSUC=1
0008       PRLOOP=540
0009       CBSSEC=2184
0010       H2SSEC=2184+1080
0011       EFSSEC=24
0012       C20=+.031142870
0013       C02=+.122494967
0014       C11=+.091107809
0015       C21=-.007675052
0016       C12=-.010228481
0017       C30=-.002924285
0018       C03=-.008226780
C
C
C REQUEST INFORMATION AND CALCULATE CONSTANTS
C
0019       WRITE(5,8)
0020   8   FORMAT(//,1H$,'CALIBRATION COEFFICIENT = ')
0021       READ(5,2)CCOEF
0022   2   FORMAT(I6)
0023       C=FLOAT(CCOEF)
0024       WRITE(5,11)
0025   11  FORMAT(1H$,'SYSTEM COEFFICIENT = ')
0026       READ(5,2)CSYS
0027       CS=FLOAT(CSYS)
0028       WRITE(5,20)
0029   20  FORMAT(1H$,'    EFFICIENT OF C**2= ')
0030       READ(5,30)A
0031   30  FORMAT(F10.9)
0032       C20=(C20-A)*CS
0033       C02=(C02-A)*CS
0034       C11=(C11-2.0*A)*CS
0035       C21=C21*CS
0036       C12=C12*CS
0037       C30=C30*CS
0038       C03=C03*CS
C
C
C INITIALIZE DK1: AND I/O PARAMETERS
C
0039       CALL ASNLUN(IDISK,'DK',1)
0040       IPARAM(2)=512*2
0041       JPARAM(2)=512*2
0042       KPARAM(2)=512*2
```

```
0043            CALL GETADR(IPARAM,PRJCB)
0044            CALL GETADR(JPARAM,PRJH2O)
0045            CALL GETADR(KPARAM,ERRORF)
0046            IPARAM(5)=CBSSEC
0047            JPARAM(5)=H2SSEC
0048            KPARAM(5)=EFSSEC
       C
       C
       C READ IN 1 BONE AND 1 SOFT TISSUE PROJECTION
       C
0049   100      CALL QIO(IORLB,IDISK,IEFN,,IOSB,IPARAM,IDSW)
0050            CALL WAITFR(IEFN,IDSW)
0051            IF(IOSB(1).NE.ISSUC) GO TO 970
0053            IPARAM(5)=IPARAM(5)+2
0054            CALL QIO(IORLB,IDISK,IEFN,,IOSB,JPARAM,IDSW)
0055            CALL WAITFR(IEFN,IDSW)
0056            IF(IOSB(1).NE.ISSUC) GO TO 980
0058            JPARAM(5)=JPARAM(5)+2
       C
       C
       C COMBINE PROJECTIONS
       C
0059            DO 210 I=1,511
0060            CB=FLOAT(PRJCB(I))/C
0061            CBSQRD=CB*CB
0062            CBCUBD=CB*CBSQRD
0063            H2=FLOAT(PRJH2O(I))/C
0064            H2SQRD=H2*H2
0065            H2CUBD=H2*H2SQRD
0066            Z=C20*H2SQRD + C02*CBSQRD + C11*CB*H2 + C21*H2SQRD*CB
              *    + C12*H2*CBSQRD + C30*H2CUBD + C03*CBCUBD
0067            ERRORF(I)=INT(Z)
0068   210      CONTINUE
0069            ERRORF(512)=0
       C
       C
       C WRITE OUT 1 ERROR PROJECTION
       C
0070            CALL QIO(IOWLB,IDISK,IEFN,,IOSB,KPARAM,IDSW)
0071            CALL WAITFR(IEFN,IDSW)
0072            IF(IOSB(1).NE.ISSUC) GO TO 990
0074            KPARAM(5)=KPARAM(5)+2
       C
       C
       C GET NEXT PROJECTION
       C
0075            PRLOOP=PRLOOP-1
0076            IF(PRLOOP.NE.0) GO TO 100
0078            GO TO 1000
       C
       C
       C I/O ERROR MESSAGES
       C
0079   970      JPARAM(5)=IPARAM(5)
0080   980      WRITE(5,981) IOSB(1),JPARAM(5)
0081   981      FORMAT(3X,'ERROR ',I4,' ENCOUNTERED WHILE READING SECTOR',I5)
0082            GO TO 1000
0083   990      WRITE(5,991) IOSB(1),KPARAM(5)
0084   991      FORMAT(3X,'ERROR ',I4,' ENCOUNTERED WHILE WRITING SECTOR',I5)
       C
       C
       C EXIT
       C
0085   1000     STOP
0086            END
```

TABLE VII

```
C FILT3
C PROGRAM TO PERFORM 3-POINT EQUAL-WEIGHTING FILTER
C TO ERROR (OR POSSIBLY OTHER) PROJECTIONS.
C
C
C
0001          DIMENSION IG(512)
0002          DIMENSION G(512)
0003          DIMENSION IGOUT(512)
0004          DIMENSION IOSB(2),JPARAM(6),IDSW(1)
       C
0005          IOATT=256*3
0006          IOWLB=256*1
0007          IODET=256*4
0008          IORLB=256*2
0009          IEFN1=1
0010          IDISK=2
0011          JRECSZ=1024
0012          JPARAM(2)=JRECSZ
0013          CALL GETADR(JPARAM,IG)
       C
0014          WRITE(5,20)
0015    20    FORMAT('$ISSEC=')
0016          READ(5,22)ISSEC
0017    22    FORMAT(I7)
0018          WRITE(5,23)
0019    23    FORMAT('$NPROJS=')
0020          READ(5,22)NPROJS
       C
0021          ISBLCK=ISSEC
       C
0022          DO 1000 IPR=1,NPROJS
0023          JPARAM(5)=ISBLCK+2*(IPR-1)
0024          CALL QIO(IORLB,IDISK,IEFN1,,IOSB,JPARAM,IDSW)
0025          CALL WAITFR(IEFN1,IDSW)
       C
0026          DO 200 IL=1,511
0027   200    G(IL)=FLOAT(IG(IL))
0028          IGOUT(1)=IG(1)
0029          IGOUT(511)=IG(511)
0030          IGOUT(512)=0
       C
0031          DO 500 IL=2,510
0032          GAVE=(G(IL-1)+G(IL)+G(IL+1))/3.
0033          IGOUT(IL)=IFIX(GAVE)
0034   500    CONTINUE
0035          DO 600 IT=2,510
0036   600    IG(IT)=IGOUT(IT)
       C
0037          CALL QIO(IOWLB,IDISK,IEFN1,,IOSB,JPARAM,IDSW)
0038          CALL WAITFR(IEFN1,IDSW)
0039  1000    CONTINUE
0040          STOP
0041          END
```

TABLE VIII

```
      C INTRPF
      C PROGRAM TO INTERPRETIVELY FILTER PROJECTIONS (MADE BY UNMFB OR ITERIM)
      C

0001          DIMENSION IG(512)
0002          DIMENSION G(512)
0003          DIMENSION IGOUT(512)
0004          DIMENSION IOSB(2),JPARAM(6),IDSW(1)
      C
0005          IOATT=256*3
0006          IOWLB=256*1
0007          IODET=256*4
0008          IORLB=256*2
0009          IEFN1=1
0010          IDISK=2
0011          JRECSZ=1024
0012          JPARAM(2)=JRECSZ
0013          CALL GETADR(JPARAM,IG)
      C
0014          WRITE(5,20)
0015   20     FORMAT('$ISSEC=')
0016          READ(5,22) ISSEC
0017   22     FORMAT(I7)
0018          WRITE(5,23)
0019   23     FORMAT('$NPROJS=')
0020          READ(5,22)NPROJS
0021          WRITE(5,24)
0022   24     FORMAT('$THRESH=')
0023          READ(5,26)THRESH
0024          WRITE (5,25)
0025   25     FORMAT('$IDMAX=')
0026          READ (5,22)IDMAX
0027   26     FORMAT(F16.7)
      C
0028          ISBLCK=ISSEC
      C
0029          DO 1000 IPR=1,NPROJS
0030          JPARAM(5)=ISBLCK+2*(IPR-1)
0031          CALL QIO(IORLB,IDISK,IEFN1,,IOSB,JPARAM,IDSW)
0032          CALL WAITFR(IEFN1,IDSW)
      C
0033          DO 200 IL=1,511
0034   200    G(IL)=FLOAT(IG(IL))
      C
      C
0035          IGOUT(1)=IFIX(G(1))
0036          IGOUT(2)=IFIX((G(1)+G(2)+G(3))/3.)
0037          IGOUT(511)=IFIX(G(511))
      C
      C PUT IN WILD DATA VALUE AT END TO STOP SEARCHING AT 511TH POINT.
0038          C(512)=10.**12
      C
      C FAKE PREVIOUS SUM AND DELTA L:
0039          SUM=G(1)+G(2)+G(3)
0040          ID=1
      C
0041          DO 500 IL=3,510
0042          GCTR=G(IL)
      C CALCULATE UP TO 3 "TRIAL" SMOOTHINGS
      C AND USE THE AVERAGE CALCULATED FROM THE LARGEST DOMAIN WHICH
      C SATISFIES THE DIFFERENCE THRESHOLD CONDITION; IF NONE OF THE
      C THREE POSSIBLE SMOOTHED VALUES SATISFIES THIS CONDITION,
      C USE THE SMALLEST INTERVAL. IN ANY CASE, DON'T LET THE INTERVAL
      C SIZE DROP BELOW 3 POINTS.
      C
      C CASE 1. LEFT LIMIT STAYS SAME; RIGHT MOVES RIGHT BY 2:
0043          IF (ID.EQ.IDMAX) GO TO 300
0045          SUM1=SUM+G(IL+ID)+G(IL+ID+1)
0046          G1=SUM1/(FLOAT(2*ID+3))
0047          D1=ABS(G1-GCTR)
0048          IF (D1.LT.THRESH) GO TO 401
```

```
C CASE2. TRY MOVING BOTH LEFT & RIGHT LIMITS RIGHT BY 1:
0050   300   SUM2=SUM+C(IL+ID)-C(IL-ID-1)
0051         C2=SUM2/FLOAT(2*ID+1)
0052         D2=ABS(C2-CCTR)
0053         IF (D2.LT.THRESH) GO TO 402
C CASE3. TRY MOVING LEFT LIMIT RIGHT BY 2 & LEAVING RIGHT LIMIT ALONE:
0055         IF (ID.EQ.1) GO TO 404
0057         SUM3=SUM-C(IL-ID)-C(IL-ID-1)
0058         C3=SUM3/FLOAT(2*ID-1)
0059         SUM=SUM3
0060         ICOUT(IL)=IFIX(C3)
0061         ID=ID-1
0062         GO TO 500
       C
0063   401   SUM=SUM1
0064         ICOUT(IL)=IFIX(C1)
0065         ID=ID+1
0066         GO TO 500
0067   402   SUM=SUM2
0068         ICOUT(IL)=IFIX(C2)
0069         GO TO 500
C SPECIAL CASE TO HANDLE ID=1 WHILE THRESH NOT SATISFIED:
0070   404   SUM=C(IL-1)+C(IL)+C(IL+1)
0071         ICOUT(IL)=IFIX(SUM/3.)
0072   500   CONTINUE
       C
0073         DO 600 ITMP=1,511
0074   600   IC(ITMP)=ICOUT(ITMP)
0075         CALL QIO(IOWLB,IDISK,IEFN1,,IOSB,JPARAM,IDSW)
0076         CALL WAITFR(IEFN1,IDSW)
0077   1000  CONTINUE
0078         STOP
0079         END
```

TABLE IX

```
C COMBIM
C
C
C PROGRAM TO ADD 2
C IMAGE FILES TOGETHER
C WITH THE OPTION OF
C MULTIPLYING ONE OF
C THE IMAGE FILES BY
C A WEIGHTING CONSTANT
C
C
C
C
C
C
C FOR COMBIM,LP/SP=COMBIM
C TKB COMBIM=COMBIM
C    /
C    MAXBUF=512
C    UIC=[100,100]
C
C
C
0001         DIMENSION   ORIG(256),ERRR(256),CORR(256)
0002         INTEGER     ORIG,CORR,ORGIMG,ERRIMG,ORGSEC,
            *            ERRSEC,CORSEC,SECTLP,ERRR
0003         SECTLP=256
       C
       C
       C REQUEST INFORMATION
       C
0004   1     WRITE(5,2)
0005   2     FORMAT(//,1H$,' NUMBER OF SECTORS IN ORIG.IMG;1 (256 OR 258) = ')
0006         READ(5,3)ORGIMG
0007   3     FORMAT(I6)
0008         IF(ORGIMG.NE.256.AND.ORGIMG.NE.258) GO TO 1
0010         ORGSEC=1
0011   11    WRITE(5,12)
```

```
0012   12    FORMAT(1H$,' NUMBER OF SECTORS IN ERROR.IMG;1 (256 OR 258) = ')
0013         READ(5,3)ERRIMG
0014         IF(ERRIMG.NE.256.AND.ERRIMG.NE.258) GO TO 11
0016         ERRSEC=1
0017         IF(ERRIMG.EQ.258)ERRSEC=3
0019         WRITE(5,22)
0020   22    FORMAT(1H$,' WEIGHTING CONSTANT = ')
0021         READ(5,23)WC
0022   23    FORMAT(F6.4)
0023         CORSEC=1
C
C
C  INITIALIZE FILES AND WRITE OUT HEADER IF NECESSARY
C
0024         CALL ASSIGN(1,'ORIG.IMG;1')
0025         CALL ASSIGN(2,'ERROR.IMG;1')
0026         CALL ASSIGN(3,'CORR.IMG;1')
0027         DEFINE FILE 1(ORGIMG,256,U,IV1)
0028         DEFINE FILE 2(ERRIMG,256,U,IV2)
0029         DEFINE FILE 3(ORGIMG,256,U,IV3)
0030         IF(ORGIMG.EQ.256) GO TO 150
0032         READ(1'ORGSEC,ERR=970)(ORIG(I),I=1,256)
0033         WRITE(3'CORSEC,ERR=980)(ORIG(I),I=1,256)
0034         ORGSEC=ORGSEC+1
0035         CORSEC=CORSEC+1
0036         READ(1'ORGSEC,ERR=970)(ORIG(I),I=1,256)
0037         WRITE(3'CORSEC,ERR=980)(ORIG(I),I=1,256)
0038         ORGSEC=ORGSEC+1
0039         CORSEC=CORSEC+1
0040   150   CONTINUE
C
C
C READ IN 1 SECTOR OF ORIG.IMG;1 AND ERROR.IMG;1
C
0041   200   READ(1'ORGSEC,ERR=970)(ORIG(I),I=1,256)
0042         ORGSEC=ORGSEC+1
0043         READ(2'ERRSEC,ERR=975)(ERRR(I),I=1,256)
0044         ERRSEC=ERRSEC+1
C
C
C COMBINE 2 IMAGES PIXEL BY PIXEL
C
0045         DO 300    I=1,256
0046         Z=(WC*FLOAT(ERRR(I)))+FLOAT(ORIG(I))+.5
0047   300   CORR(I)=Z
C
C
C WRITE OUT 1 SECTOR OF CORRECTED IMAGE
C
0048         WRITE(3'CORSEC,ERR=980)(CORR(I),I=1,256)
0049         CORSEC=CORSEC+1
C
C
C GET NEXT SECTOR
C
0050         SECTLP=SECTLP-1
0051         IF(SECTLP.NE.0) GO TO 200
0053         GO TO 1000
C
C
C I/O ERROR MESSAGES
C
0054   970   WRITE(5,971)ORGSEC
0055   971   FORMAT(3X,'ERROR WHILE READING SECTOR ',I4,' OF ORIG.IMG;1')
0056         GO TO 1000
0057   975   WRITE(5,976)ERRSEC
0058   976   FORMAT(3X,'ERROR WHILE READING SECTOR ',I4,' OF ERROR.IMG;1')
0059         GO TO 1000
0060   980   WRITE(5,981)CORSEC
0061   981   FORMAT(3X,'ERROR WHILE WRITING SECTOR ',I4,' OF CORR.IMG;1')
C
C
C EXIT
C
0062   1000  STOP
```

I claim:

1. A computerized tomographic system for measuring characteristics of and imaging, body tissue comprising:
   scanning means which generate projections of said tissue by directing a known spectrum of radiation through said body and measuring the spatial intensity distribution of radiation traversing said tissue along a multiplicity of paths;
   image generating means which calculate the attenuation of each pixel element of a raw image array, which is representative of a tranverse section of said tissue, from said projections;
   means which analyze values in said raw image array and assign to each pixel element, on the basis of those values, a specific proportion of the attenuation coefficient to each of two or more constituents of said tissue;
   means which combine said element proportions to generate a multiplicity of constituent projections for each of said constituents of said tissue;
   means which combine said constituent projections, in accordance with a predetermined function approximating the non-linear interaction of said constituents with said spectral intensity distribution, to generate a multiplicity of error projections of said tissue;
   means which combine said error projections to generate an error image array which is representative of the polychromatic aberration in said raw image array; and
   means for subtracting said error image array from said raw image array to generate a compensated image array.

2. The system of claim 1 wherein said predetermined function is a multidimensional polynomial.

3. The system of claim 1 wherein said constituents are bone and soft tissue and said function is a two-dimensional cubic.

4. The system of claim 1 wherein said means which analyze and assign function by thresholding and interpolating the values of said elements relative to the thresholds.

5. The system of claim 1 further including means for filtering said error projections.

6. A system for compensating polychromatic distortion in a computed tomographic image of body tissue comprising:
   means for generating an error image wherein the numerical value of each image element is representative of the polychromatic distortion in a corresponding element of said tomographic image which means include means for producing constituent projections of each of at least two constituents of said tissue from said tomographic image and means for combining said constituent projections to generate said error image and
   means for subtracting said error image, element by element, from said tomographic image.

7. The system of claim 6 wherein said means for producing constituent projections include means for assigning a proportion of each element of said tomographic image to each of said constituents.

8. The system of claim 7 wherein said means for assigning a proportion compare the value of each element with predetermined threshold values and assign said proportions on the basis of said comparison.

9. The system of claim 8 wherein said means for assigning determined said proportion by interpolating each element value between threshold values.

10. The system of claim 7 wherein said means for producing constituent projections include, for each of said projections, means for associating each of said elements with one of a multiplicity of image strips and
    means for summing each of the constituent proportion values for all elements associated with each strip whereby said proportion values are projected along said strips.

11. The system of claim 6 wherein said means for combining constituent projections functions to combine said constituent projections in accordance with a multidimensional polynomial the coefficients of which are determined from a least-squares approximation of the interaction of radiation, having the same spectral content as was used to measure said tomographic image, with the spectral radiation absorption characteristics of said constituents.

12. The system of claim 11 wherein said constituents are bone and soft tissue and said multidimensional polynomial is a two-dimensional cubic.

13. The system of claim 11 further including filter means which function to filter the output of said means for combining said constituent projections.

14. A method for measuring characteristics of, and imaging, body tissue comprising the steps of:
    directing a known spectrum of radiation through said tissue;
    measuring the spatial intensity distribution of said radiation traversing said tissue along a multiplicity of paths;
    generating a multiplicity of projections of said tissue from said spatial intensity distribution;
    calculating, from said projections, an attentuation value for each element of a raw image, said raw image being representative of a transverse section of said tissue and each element of said raw image corresponding to a distinct portion of said tissue;
    for each of said elements of said raw image, comparing the associated attenuation value with a threshold value and, on the basis of the result of said comparison, assigning a proportion of the associated attenuation value to each of two or more constituents of the tissue;
    for each of said constituents of the tissue, combining the associated proportions of the attenuation values associated with all of said elements to generate a multiplicity of constituent projections of said tissue;
    combining said constituent projections, in accordance with a predetermined function approximating the non-linear interaction of said constituents with said known spectrum of radiation, to generate a multiplicity of error projections of said tissue;
    combining said error projections to generate an error image which is representative of the polychromatic aberration in said raw image; and
    subtracting said error image from said raw image to generate a compensated image.

15. The method of claim 14 wherein said predetermined function is a multidimensional polynomial.

16. The method of claim 14 wherein said constituents are bone and soft tissue and said function is a two-dimensional cubic.

* * * * *